US006969783B2

(12) United States Patent (10) Patent No.: US 6,969,783 B2
Hannah et al. (45) Date of Patent: Nov. 29, 2005

(54) HEAT STABLE MUTANTS OF STARCH BIOSYNTHESIS ENZYMES

(75) Inventors: L. Curtis Hannah, Gainesville, FL (US); Thomas W. Greene, Zionsville, IN (US); Brian Burger, Oldsmar, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 212 days.

(21) Appl. No.: 10/099,031

(22) Filed: Mar. 14, 2002

(65) Prior Publication Data

US 2003/0056248 A1 Mar. 20, 2003

Related U.S. Application Data

(60) Provisional application No. 60/275,768, filed on Mar. 14, 2001.

(51) Int. Cl.[7] .................. C12N 15/82; C12N 15/29; C12N 15/54; A01H 5/00; A01H 5/10

(52) U.S. Cl. .................. 800/284; 800/278; 800/289; 800/312; 800/317.2; 800/320; 800/320.1; 800/320.2; 800/320.3; 435/194; 536/23.2; 536/23.6

(58) Field of Search .................. 800/278, 284, 800/289, 312, 317.2, 320–320.3, 306, 305, 315, 321; 435/194; 536/23.2, 23.6

(56) References Cited

U.S. PATENT DOCUMENTS

| 5,498,831 A | 3/1996 | Burgess et al. |
| 5,589,618 A | 12/1996 | Hannah et al. |
| 5,650,557 A | 7/1997 | Hannah et al. |
| 5,712,135 A | 1/1998 | D'Halluin et al. |
| 5,773,693 A | 6/1998 | Burgess et al. |
| 5,872,216 A | 2/1999 | Hannah et al. |
| 5,977,437 A | 11/1999 | Villand et al. |
| 6,013,861 A | 1/2000 | Bird et al. |
| 6,069,300 A | 5/2000 | Hannah et al. |
| 6,096,945 A | 8/2000 | Burrell et al. |
| 6,379,968 B1 | 4/2002 | Poulsen |
| 6,403,863 B1 | 6/2002 | Hannah et al. |
| 6,483,011 B1 | 11/2002 | Stemmer et al. |
| 6,486,383 B1 | 11/2002 | Burrell et al. |
| 2002/0194642 A1 | 12/2002 | Hannah et al. |

FOREIGN PATENT DOCUMENTS

| EP | 455316 A2 | 4/1991 |
| WO | WO 94/09144 A1 | 4/1994 |
| WO | WO 94/11520 A2 | 5/1994 |
| WO | WO 94/24292 A2 | 10/1994 |
| WO | WO 95/34660 A1 | 12/1995 |
| WO | WO 97/42326 A2 | 11/1997 |
| WO | WO 98/22601 A1 | 5/1998 |
| WO | WO 99/58698 A2 | 11/1999 |
| WO | WO 01/64928 A2 | 9/2001 |

OTHER PUBLICATIONS

Ainsworth, C. et al. "Adenosine Diphosphate Glucose Pyrophosphorylase Genes in Wheat: Diferential Expression and Gene Mapping" *Planta*, 1995, Accession No. S60572.

Anderson, J. M. et al. "The Encoded Primary Sequence of a Rice Seed ADP–glucose Pyrophosphorylase Subunit and its Homology to the Bacterial Enzyme" *J. Biological Chemistry*, 1989, pp. 12238–12242, vol. 264, No. 21.

Anderson, J. M. et al. "Molecular Characterization of the Gene Encoding a Rice Endosperm–Specific ADPglucose Pyrophosphorylase Subunit and its Development Pattern of Transcription" *Gene*, 1991, pp. 199–205, vol. 97.

Badu–Apraku, B. et al. "Effect Of Temperature During Grain Filling On Whole Plant And Grain Yield in Maize (*Zea mays* L.)" *Can. J. Plant Sci.*, 1983, pp. 357–363, vol. 63.

Bae, M. M. et al. "Cloning And Characterization Of The Brittle–2 Gene Of Maize" *Maydica*, 1990, pp. 317–322, vol. 35.

Ballicora et al. "Adenosine 5'–Diphosphate–Glucose Pyrophosphorylase from Potato Tuber" *Plant Physiol.*, 1995, pp. 245–251, vol. 109.

Bhave, M. R. et al. "Identification and Molecular Characterization of Shrunken–2 cDNA Clones of Maize" *The Plant Cell*, 1990, pp. 581–588, vol. 2.

Bhave, M. R. et al. "Identification and Molecular Characterization of Shrunken–2 cDNA Clones of Maize" *Plant Cell*, 1990, Accession No. P55241.

Bowie, J. U. et al., "Deciphering the Message in Protein Sequences: Tolerance to Amino Acid Substitutions" *Science*, 1990, pp. 1306–1310, vol. 247.

Broun, P. et al. "Catalytic Plasticity of Fatty Acid Modification Enzymes Underlying Chemical Diversity of Plant Lipids" *Science*, 1998, pp. 1315–1317, vol. 282.

(Continued)

*Primary Examiner*—David T. Fox
(74) *Attorney, Agent, or Firm*—Saliwanchik, Lloyd & Saliwanchik

(57) ABSTRACT

The subject invention pertains to novel mutant polynucleotide molecules that encode enzymes that have increased heat stability. These polynucleotides, when expressed in plants, result in increased yield in plants grown under conditions of heat stress. In one embodiment, the polynucleotide molecules of the subject invention encode maize endosperm ADP glucose pyrophosphorylase (AGP) activity. Plants and plant tissue bred to contain, or transformed with, the mutant polynucleotides, and expressing the polypeptides encoded by the polynucleotides, are also contemplated by the present invention. The subject invention also concerns methods for isolating polynucleotides and polypeptides contemplated within the scope of the invention. Methods for increasing yield in plants grown under conditions or heat stress are also provided.

38 Claims, 9 Drawing Sheets

OTHER PUBLICATIONS

Chang, Jen–Hu "Corn Yield In Relation To Photoperiod, Night Temperature, And Solar Radiation" *Agricultural Meterology*, 1981, pp. 253–262, vol. 24.

Charng, Y. Y. et al. "Structure–Function Relationships of Cyanobacterial ADP–glucose Pyrophosphorylase" *J. Biol. Chem.*, 1994, pp. 24107–24113, vol. 269, No. 39.

Cheikh, N. et al. "Heat Stress Effects on Sink Activity of Developing Maize Kernels Grown In Vitro" *Physiologia Plantarium*, 1995, pp. 59–66, vol. 95.

Conroy, J. P. et al. "Influence of Rising Atmospheric $CO_2$ Concentrations and Temperature on Growth, Yield and Grain Quality of Cereal Crops" *Aust. J. Plant Physiol.*, 1994, pp. 741–758, vol. 21.

Copeland, L. et al. "Purification of Spinach Leaf ADPglucose Pyrophosphorylase" *Plant Physiol.*, 1981, pp. 996–1001, vol. 68.

Denyer, K. et al., "The Effect of High Temperature on Starch Synthesis and the Activity of Starch Synthase" *Aust. J. Plant Physiol.*, 1994, pp. 783–789, vol. 21.

Dickinson, D. B. et al. "Presence of ADP–Glucose Pyrophosphorylase in Shrunken–2 and Brittle–2 Mutants of Maize Endosperm" *Plant Physiol.*, 1969, pp. 1058–1062, vol. 44.

Duke, E. R. et al. "Effects Of Heat Stress On Enzyme Activities And Transcript Levels In Developing Maize Kernels Grown In Culture" *Environmental and Experimental Botany*, 1996, pp. 199–208, vol. 36, No. 2.

Giroux, M. J. et al. "A Single Gene Mutation That Increases Maize Seed Weight" *Proc. Natl. Acad. Sci. USA*, 1996, pp 5824–5829, vol. 93.

Greene, T. W. et al. "Mutagenesis of the Potato ADPglucose Pyrophosphorylase and Characterization of an Allosteric Mutant Defective in 3–phosphoglycerate Activation" *Proc. Natl Acad. Sci. USA*, 1996, pp. 1509–1513.

Greene, T. W. et al. "Aspartic Acid 413 is Important for the Normal Allosteric Functioning of ADP–Glucose Pyrophosphorylase" *Plant Physiol.*, 1996, pp. 1315–1320, vol. 112.

Greene, T. W. et al. "Enhanced Stability of Maize Endosperm ADP–glucose Pryophosphorylase is Gained Through Mutants that After Subunit Interactions" *Proc. Natl. Acad. Sci. USA*, 1998, pp. 13342–13347, vol. 95.

Greene, T.W. et al. "Generation of Up–regulated Allosteric Variants of Potato ADP–glucose Pyrophosphorylase by Reversion Genetics" *Proc. Natl. Acad. Sci. USA*, 1998, pp. 10322–10327, vol. 95.

Hannah, L. C. et al. "Characterization of Adenosine Diphosphate Glucose Pyrophosphorylases from Developing Maize Seeds" *Plant Physiol.*, 1975, pp. 297–302, vol. 55.

Hannah, L. C. "Starch Synthesis in the Maize Seed" In *Cellular and Molecular Biology of Plant Seed Development*, 1997, pp. 375–405, B.A. Larkins and I.K. Vasil (eds.), Kluwer Academic Publishers, printed in the Netherlands.

Hannah, L. C. et al. "Characterization of ADP–Glucose Pyrophosphorylase from Shrunken–2 and Brittle–2 Mutants of Maize" *Biochemical Genetics*, 1976, pp. 547–560, vol. 14, Nos. 7/8.

Hannah, L. C. et al. "Multiple Forms Of Maize Endosperm ADP–Glucose Pyrophosphorylase And Their Control By Shrunken–2 and Brittle–2" *Genetics*, 1980, pp. 961–970, vol. 95.

Hawker, J. S. et al. "High Temperature Affects the Activity of Enzymes in the Committed Pathway of Starch Synthesis in Developing Wheat Endosperm" *Aust. J. Plant Physiol.*, 1993, pp. 197–209, vol. 20.

Iglesias et al. "Expression of the Potato Tuber ADP–glucose Pyrophosphorylase in *Escherichia coli*" *J. of Biological Chemistry*, 1993, pp. 1061–1086, vol. 268, No. 2.

Jenner, C. F. "Starch Synthesis in the Kernel of Wheat Under High Temperature Conditions" *Aust. J. Plant Physiol.*, 1994, pp. 791–806, vol. 21.

Jenner, C. F. et al. "Thermal Characteristics of Soluble Starch Synthase from Wheat Endosperm" *Aust. J. Plant Physiol.*, 1995, pp. 703–709, vol. 22.

Jensen, L. G. et al. "Transgenic Barley Expressing a Protein–Engineered, Thermostable $(1,3-1,4)-\beta$–Glucanase During Germination" *Proc. Natl. Acad. Sci. USA*, 1996, pp. 3487–3491, vol. 93.

Jones, R. J. et al. "Temperature Effects On In Vitro Kernel Development of Maize" *Crop Science*, 1981, pp. 761–766, vol. 21.

Jones, R. J. et al. "Thermal Environment During Endosperm Cell Division And Grain Filling In Maize: Effects On Kernel Growth And Development In Vitro" *Crop Science*, 1964, pp. 133–137, vol. 24.

Keeling, P. L. et al. "Elevated Temperature Reduces Starch Deposition in Wheat Endosperm by Reducing the Activity of Soluble Starch Synthase" *Planta*, 1993, pp. 342–348, vol. 191.

Kim, C. H. et al. "Heat–resistant ADP–glucose Pyrophosphorylase Produced from Thermas Caldophilus sp." *Korea Adv. Inst. Sci. & Techology*, 1998, XP–002127965 (abstract only).

Lafta, A. M. et al. "Effect of High Temperature on Plant Growth and Carbohydrate Metabolism in Potato" *Plant Physiology*, 1995, pp. 637–643, vol. 109.

Laughlin, M. J. et al. "N– and C–terminal Peptide Sequences are Essential for Enzyme Assembly, Allosteric, and/or Catalytic Properties of ADP–glucose Pyrophosphorylase" *The Plant Journal*, 1998, pp. 159–168, vol. 14, No. 2.

Lazar, E. et al. "Transforming Growth Factor α: Mutation of Aspartic Acid 47 and Leucine 48 Results in Different Biological Activities" *Molecular and Cellular Biology*, 1968, pp. 1247–1252, vol. 8, No. 3.

Lin, Tsan–Piao et al. "A Starch Deficient Mutant of *Arabidopsis thaliana* with Low ADPglucose Pyrophosphorylase Activity Lacks One of the Two Subunits of the Enzyme" *Plant Physiol.*, 1988, pp. 1175–1181, vol. 88.

Maniatis, T. et al. "Nuclease Ba/31" In *Enzymes Used in Molecular Cloning, A Laboratory Manual*, 1982, pp. 135–139, Cold Spring Harbor Laboratory.

Morell, M. et al. "Affinity Labeling of the Allosteric Activator Site(s) of Spinach Leaf ADP–glucose Pyrophosphorylase" *J. Biological Chemistry*, 1988, pp. 633–637, vol. 263, No. 2.

Muller–Rober et al. "One of Two Different ADP–glucose Pyrophosphorylase Genes From Potato Responds Strongly to Elevated Levels of Sucrose" *Mol Gen Genet*, 1990, pp. 136–146, vol. 224.

Nakata, P. A. et al. "Comparison of the Primary Sequences of Two Potato Tuber ADP–glucose Pyrophosphorylase Subunits" *Plant Molecular Biology*, 1991, pp. 1089–1093, vol. 17.

Okita, T. W. et al. "The Subunit Structure of Potato Tuber ADPglucose Pyrophosphorylase" *Plant Physiol.*, 1990, pp. 785–790, vol. 93.

Okita, T. W. et al. "Engineering Plant Starches by the Generation of Modified Plant Biosynthetic Enzymes" In *Engineering Crops for Industrial End Uses*, Shewry, P.R., Napier, J.A., and Davis, P., eds., 1998, pp. 1–18, Portland Press Ltd., London.

Olive, M. R. et al. "Isolation and Nucleotide Sequences of cDNA Clones Encoding ADP–glucose Pyrophosphorylase Polypeptides from Wheat Leaf and Endosperm" *J. Molecular Biology*, 1989, pp. 525–538, vol. 12.

Ou–Lee, Tsai–Mel et al. "Effect of Increased Temperature in Apical Regions of Maize Ears on Starch–Synthesis Enzymes and Accumulation of Sugars and Starch" *Plant Physiol.*, 1985, pp. 852–855, vol. 79.

Preiss, J. et al. "Molecular Biology and Regulatory Aspects of Glycogen Biosynthesis in Bacteria" *Progress in Nuc. Acid Res. and Mol Biol.*, 1994, pp. 299–329, vol. 47.

Preiss, J. et al. "Starch Synthesis in Sinks and Sources" In *Photoassimilate distribution in plants and crops: Source–sink relationships*, Zamski, E. and Schaffer, A.A., ed., 1996, pp. 1–63, Marcil Dekker Inc.

Preiss, J. "Bacterial Glycogen Synthesis and Its Regulation" *Ann. Rev. Microbiol.*, 1984, vol. 38, pp. 419–458.

Rijven, A.H.G.C. "Heat Inactivation of Starch Synthase in Wheat Endosperm Tissue" *Plant Physiol.*, 1986, pp. 448–453, vol. 81.

Satozawa, T. et al. "Direct Submission", 1995, Accession No. T02965.

Shaw, J. R. et al. "Genomic Nucleotide Sequence of a Wild–Type Shrunken–2 Allele of *Zea mays*" *Plant Physiol.*, 1992, pp. 1214–1216, vol. 98.

Singletary, G. W. et al. "Decreased Starch Synthesis in Heat Stessed Maize Kernels Results From Reduced ADPG–Pyrophosphorylase And Starch Synthase Activities" *Plant Physiol.*, 1993, vol. 102, No. 6(suppl) abstract.

Singletary, G. W. et al. "Heat Stress During Grain Filling in Maize: Effects on Carbohydrate Storage and Metabolism" *Aust. J. Plant Physiol.*, 1994, pp. 829–841, vol. 21.

Smith–White, B. J. et al. "Comparison of Proteins of ADP–Glucose Pyrophosphorylse from Diverse Sources" *J. Mol. Evol.*, 1992, pp. 449–464, vol. 34.

Sowokinos, J. R. et al. "Pyrophosphorylases in *Solanum tuberosum*" *Plant Physiol.*, 1982, pp. 1459–1466, vol. 69.

Stark, D. M. et al. "Regulation of the Amount of Starch in Plant Tissues by ADP Glucose Phyrophosphorylase" *Science*, 1992, pp. 287–292, vol. 258.

Suzuki, D. T. et al. "Mechanisms of Genetic Change I: Gene Mutation" 4th edition, 1989, pp. 476–499, W. H. Freeman and Company, New York.

Sweetlove, L. J. et al. "Starch Metabolism in Tubers of Transgenic Potato (*Solanum tuberosum*) with Increased ADPglucose Pyrophosphorylase" *Biochem. J.*, 1996, pp. 493–498, vol. 320.

Thompson, Louis M. "Weather Variability, Climate Change, and Grain Production" *Science*, 1975, pp. 535–541, vol. 188.

Thompson, Louis M. "Climate Change, Weather Variability, and Corn Production" *Agron. J.*, 1986, pp. 649–653, vol. 78.

Tollenaar, M. et al. "Effects of Temperature On Rate And Duration Of Kernel Dry Matter Accumulation Of Maize" *Can. J. Plant Sci.*, 1988, pp. 935–940, vol. 68.

Tsai, C. Y. et al. "Starcy–Deficient Maize Mutant Lacking Adenosine Diphosphate Glucose Pyrophosphorylase Activity" *Science*, 1966, pp. 341–343, vol. 151.

Villand, P. et al. "ADP–glucose Pyrophosphorylase Large Subunit from Barley Endosperm" *Plant Mol. Biol.*, 1992, Accession No. P30524.

```
-1020  TGATGCTTTTCCTGGCAGGGAGAGCTATGAGACTATGTCCTCAAAGCCACTTTGCAT
 -960  TGTGTGAAACCAATATGATCTTGTTACTTCATCATGCATGAACATTTGTGAAACTAC
 -900  TAGCTTACAAGCATTAGTGACAGCTCAGAGAAAAAGTTATCTCTGAAAGGTTTCATGTGTA
 -840  CCGTGGGAAATGAGAGAAAGTTGCCAACTCAAACACCTTCAATATGTTGTTTGCAGGCAAA
 -780  CTCTTCTGGAAGAAAGGTGTCTAAAACTATGAACGGGTTACAGAAAGGTATAAACCACGG
 -720  CTGTGCATTTGGAAGTATCATCTATAGATGTCTGTTGAGGGGAAAGCCGTACGCCAACG
 -660  TTATTACTCAGAAACAGCTTCAACACAGTTGTCTGCTTTATGATGGCATCTCCACCC
 -600  AGGCACCCACCATCACCTATTCCACCTTCCTGTTATTTCTTGCCCTTTCT
 -540  GATCATAAAAATCATTAAGAGTTTGCAAACATGCATAGCATATCAATATGCTCATTTA
 -480  TTAATTTGCTAGCAGATCATCTTCCTACTCTTTATTTATTGTTGAAAATATGT
 -420  CCTGCACCTAGGGAGCTCGTATACAGAGTATTTTCAAAATTAATTAGCGGCTTCTATATGTTT
 -360  AAGGAAGTAGGAACCTATGAGGGCAAGGCAAAATCGGAACACTAATGATGGTTGGTTGCATGAGTCTGTCG
 -300  ATAGCAAAGGCCAAGGCAAATGTGAACCTTTGTTCTGTGCCGTGGGCATAAAAACAACAGCTTCT
 -240  ATTACTTGCAAGAAATGTGAACTTGCACTTGCAAGAATGTGAACTCCTTTTTCATTTCTGTATGT
 -180  AGCCTCTTTACGGTACTTGCACTTGCAAGCATCCAGGCTTTTTCATGGTGTCTTTACACAGTTCAT
 -120  GGACATAATGCCAAAGCATGCCCCTCCTCATACTCTATATAACATCAACAGCATCGCAATTAGCC
  -60  CTCCACCAGTATGCCCCTTCGGGGAGGCAAGTGATGTTCGACCTTGCAGCCACCTTTTTTGTTCTG
    1  ACAAGATCACTTCGGGAGGCAAGTGATTCGACCTTGCAGCCACCTTTTTGTTCTG
   61  TTgtaagtatactttccctacccatcttttatctgtagttaatttgtaattgggaagta
  121  ttagtggaaagaggatgagagtgctatcatctatgtactctgcaaatgcatctgacgttat
  181  atgggctgctcatataatttgaattgctccattcttgccgacaatatattgcaaggtat
  241  atgcctagttccatcaaaagttctgtttttcattcattcttagtggcacgcaa
  301  ttttgtccatgagggaaggaaatctgttttggttacttgcttgaggtgcattcttcat
  361  atgtccagttttatggaagtaataaacttcagtttggtcatatgtcatattaaaggg
  421  caaacatatattcaattcatcgtaaatgttccctttttgtaaagattgcata
  481  ctcatttattgagttgcagGTGTATCGAGTAGTTGGAGGAGATATGCAGTTTGCACTTG
```

FIG. 1A

```
                                                                                  M   Q   F   A   L
 541  CATTGGACACGAACTCAGTTCCTCACCAGATAAGATCTTGTGAGGGTGATGGGATTGACA
       A   L   D   T   N   S   G   P   H   Q   I   R   S   C   E   G   D   G   I   D
 601  GGTTGGAAAATTAAGTATTGGGGCAGAAAGCAGGAGAAAGCTTTGAGAAATAGGTGCT
       R   L   E   K   L   S   I   G   G   R   K   Q   E   K   A   L   R   N   R   C
 661  TTGGTGGTAGAGTTGCTGCAACTACACAATGTATTCTTACCTCAGATGCTTGTCCTGAAA
       F   G   G   R   V   A   A   T   Q   C   I   L   T   S   D   A   C   P   E
 721  CTCTTgtaagtatccacctcaattattactcttactgttggttacttacgtttgtct
       T   L
 781  tttcaaggaaatttactgtattttttgtgttttgtgggagttctatacttctgttggac
 841  tggttattgtaaagatttgttcaaataggtcatctaataattgtttgaaatctgggaac
 901  tgtggttcactgcgttcaggaaaagtgaattattggttactgcatgataacttatgg
 961  aaatagaccttagagttgctgcattacatataactgcaactcctagttgcgttcaaaaaaaaa
1021  gttctttcgacctcgcattacatataactgcaactcctagttgcgttcaaaaaaaaa
1081  atgcaactcttagaacgctcaccagtgtaatctttcctgaattgttattaatgcatgt
1141  atgcactacttgtatactctaggattaagtaatctaactctaggcccatatttgca
1201  gCATTCTCAAACACAGTCCTCTAGAAAATTATGCTGATGCAAACCGTGTATCTGCTAT
       H   S   Q   T   Q   S   S   R   K   N   Y   A   D   A   N   R   V   S   A   I
1261  CATTTGGGGCGGAGGCACTGGATCTCAGCTCTTTCCTCTGACAAGCACAAGAGCTACGCC
       I   L   G   G   T   G   S   Q   L   F   P   L   T   S   T   R   A   T   P
1321  TGCTgtaagggataacactgaacatccaacgttgattactctattatagtattatacaga
       A
1381  ctgtactttttcgaattatcttagtttctacaatattagtggattctctcattttca
1441  agatacacaattgatccataatcgaagtgtatgtaagacagtgagttaaaagattatat
1501  ttttgggagacttccagtcaatttctagaagttttttggtccagatgttcataaa
```

FIG. 1B

```
1561 gtcgccgcttcatactttttaattttaattggtgcactattagGTACCTGTTGA
                                              V  P  V  G
1621 GGATGTTACAGGCTTATTGATATCCCTATGAGTAACTGCTTCAACAGTGGTATAAATAAG
      G  C  Y  R  L  I  D  I  P  M  S  N  C  F  N  S  G  I  N  K
1681 ATATTGTGATGAGTCAGTTCAATTCTACTTGCTTAACCGCCATATTCATCGTACATAC
      I  F  V  M  S  Q  F  N  S  T  S  L  N  R  H  I  H  R  T  Y
1741 CTTGAAGGCGGGATCAACTTTGCTGATGGATCTGTACAGgtgattacctcatcttgttg
      L  E  G  G  I  N  F  A  D  G  S  V  Q
1801 atgtgtaatactgtaattaggagtagatttgtgtggagaataataacagatgccgag
1861 attcttttctaaaagtctagatccaaaggcattgtggttcaaaacactatggacttctac
1921 catttatgtcattacttgccttaatgttccattgaatggggcaaattattgattctaca
1981 agtgtttaattaaaaactaattgttcatcctgcagGTATTAGCGCTACACAAATGCCTG
                                        V  L  A  A  T  Q  M  P
2041 AAGAGCCAGCTGGATGGTTCCAGGGTACAGCAGACTCTATCAGAAAATTATCTGGGTAC
      E  E  P  A  G  W  F  Q  G  T  A  D  S  I  R  K  F  I  W  V
2101 TCGAGgtagttgatatttctcgttatgaatgtccattcactcctgtagcattgt
      L  E
2161 ttctttgtaatttgagtctcctgtattctttagGATTATTACAGTCACAAATCCATT
                                       D  Y  Y  S  H  K  S  I
2221 GACAACATTGTAATCTTGAGTGGCGATCAGCTTTATCGGATGAATTACATGGAACTGTG
      D  N  I  V  I  L  S  G  D  Q  L  Y  R  M  N  Y  M  E  L  V
2281 CAGgtatggtgttcctcttgttcctcatgtttcacgtaatgtcctgatttggattaacca
      Q
2341 actactttggcatgcattatttccagAAACATGTCGAGGACGATGCTGATATCACTATA
                                K  H  V  E  D  D  A  D  I  T  I
```

FIG. 1C

```
2401  TCATGTGCTCCTGTGTTGATGAGAGgtaatcagttgttatatcatcctaatatgaatatgt
         S  C  A  P  V  D  E  S
2461  catcttgttatccaacacaggatgcatatggtctaatctgcttcctttttcccttc
2521  ggaagCCGAGCTTCTAAAAATGGGCTAGTGAAGATTGATCATACTGGACGTGTACTTCAA
         R  A  S  K  N  G  L  V  K  I  D  H  T  G  R  V  L  Q
2581  TTCTTTGAAAAACCAAAGGGTGCTGATTTGAATTCTATGgttagaaattcctgtgtaat
         F  F  E  K  P  K  G  A  D  L  N  S  M
2641  ccaattcttttgttttcctttctgagatgaacccctcttttagttattccatgg
2701  ataacctgtacttgacttattcagaaatgattttctatttgctgtagaatctgacacta
2761  aagctaatagcactgatgttgcagAGAGTTGAGACCAACTTCCTGAGCTATGCTATAGAT
                               R  V  E  T  N  F  L  S  Y  A  I  D
2821  GATGCACAGAAATATCCATACCTTGCATCAATGGGCATTTATGTCTTCAAGAAAGATGCA
         D  A  Q  K  Y  P  Y  L  A  S  M  G  I  Y  V  F  K  K  D  A
2881  CTTTTAGACCTTCTCAAgtaatcacttccctgacttattctcaactcctagttt
         L  L  D  L  L  K
2941  accttctaacagtgtcaattcttagGTCAAAATATACTCAATTACATGACTTTGGATCTG
                                  S  K  Y  T  Q  L  H  D  F  G  S
3001  AAATCCTCCCAGAGCTGTACTAGATCATAGTGTGCAGgtaagtctgatctgtctgggagt
         E  I  L  P  R  A  V  L  D  H  S  V  Q
3061  atgtgttctgtaaactgtaaattcttcatgtcaaaaagttgttttgttccagtttcca
3121  ctaccaatgcacgattatgtatttcgcttccatgcatcatcataacaatacatt
3181  ttacgtattgttagGCATGCATTTTACGGGTCATTTTACGGGAGGATGTTGAACAATCAA
                       A  C  I  F  T  G  Y  W  E  D  V  G  T  I  K
3241  ATCATTCTTTGATGCAAACTTGGCCCCTCACTGAGCAGgtactctgtcatgtattctgtac
```

FIG. 1D

```
           S   F   F   F   D   A   N   L   A   L   T   E   Q
3301   tgcatatattacctggaattcaatgcatagaatgtgttagaccatcttagttccatcc
3361   tgttttcttcaattagcttatcattaatagttgttggctagaattaaacacaaattta
3421   cctaatatgtttctctctcttcagCCTTCCAAGTTTGATTTTTACGATCCAAAACACCTTT
                              P   S   K   F   D   F   Y   D   P   K   T   P   F
3481   CTTCACTGCACCCCGATGCTTGCCTCCGACGCAATTGGACAAGTGCAAGtatatgtctt
       F   T   A   P   R   C   L   P   P   T   Q   L   D   K   C   K
3541   actgagcacaattgttacctgagcagatttttgtgtacttgactttgttctcctccacagA
3601   TGAAATATGCATTTATCTCAGATGGTTGCTTACTGAGAGAATGCAACATCGAGCATTCTG
       M   K   Y   A   F   I   S   D   G   C   L   L   R   E   C   N   I   E   H   S
3661   TGATTGGAGTCTGCTCAGTGTCAGTCTCTGGATGTGAACTCAAGtacatactctgccaa
       V   I   G   V   C   S   R   V   S   S   G   C   E   L   K
3721   tgtatctactcttgagtatccattcaacaccaagcatcaccaaatcacacagaacaat
3781   agcaacaaagcccttttagttccaagcaattagggtagcctagagttgaaatctaacaaa
3841   acaaaagtcaaagctctatacatgcaacattatctgttgaacatgtcatctttttgaatctaa
3901   tttttgggtatactacatcgcgtcttaagatcatacactagtgtcttctcccttttgccttc
3961   ccccattactacgtcttcaaaccatccaatctcaatcgtgttggacaagttttttcttgaatttgtgctacac
4021   ggacatgttcaaaccatccaatctcaatcgtgttggacaagttttttcttgaatttgtgctacac
4081   ctaacctatcacgtatgtcttcaaactctgtttcaaactctgatcctcctgtatcatcataaatcca
4141   atgcaacatacgcattatgcaacattatctgttgaacatgtcatcttttgtaggtta
4201   acattatgcaccatacaatgtacatgtccacttagaacaccatatgcttgatgccatttcatccaccc
4261   cttatgtggtatccctcttgccacttagaacaccatatgcttgatgccatttcatccaccc
4321   tgctttgattctatggctaacatcttcattaatatcctcgcctctctgtatcattggtcc

FIG. 1E
```

```
4381  taaatatggaatacacattcttctggcactacttgacccttccaaactaacgtctccttt
4441  gctcctttcttgtgtagtagtaccgaagtcacatctcatatattcggttttagtttcta
4501  ctaagtcccgggttcgatcccccgtcaggggtgaattcggctggtaaaaaatcccc
4561  tcgctgtgtcccgcccgctctcggggatcgatatcctgcgcgccaccctccggca
4621  ttgcagagtgagcagtgatcggctcgttagtgatggggagcggggttcaaggttttct
4681  cggccgggaccatgttcgttctcttaatataatgccggaggggcagtctttcccccccc
4741  ggtcgagttttagttctacgagtctaaaacctttggactctagagtccctgtcacaac
4801  tcacaactctagttttctattttctaccagcgtttatgtccctgtatgtcccttgtaatgatcactatatcgtc
4861  tgtaaaaagcatacaccaatgtaatcccctgtatgtccctgtaatattatccatcaca
4921  agaaaaaaaggtaaggctcaaagttgactttttgatatagtcctattctaatcgagaagtc
4981  atctgtatcttcgtctcttgttcgaacactagtcacaaaattttttgtacatgttcttaa
5041  tgagtccaacgtaatatccttgatatttcctttatactgtctccatcaagtcatgaaaat
5101  cacgtgtaggtccatagttcattgtttggcatgaacaaatcacacagaagttgttccttttt
5161  ctctctcatagttaaccttttgataagaggttgatcgaatctcaaggaatctgacaggtttatcaa
5221  taagatcccacacaaagaggttgatcgaatctccagcttctgtagtattgatgtaatat
5281  aatccttgtgttttcttaaactgaacacctggttcttgttactgtacccccccccc
5341  tcaatctgtttagcaagtgaacacctggttcttgttactgtacccccccccc
5401  cccccccgaggccagagttaccacgacatgaatacaagaatattgaaccagatctaga
5461  gttttgttgtactgtgaaaatcggtgacaattcatttgtttattgcgtttctgataac
5521  gacagGACTCCGTGATGATGGGAGCGGACACCTATGGGAATGAAGAAGAAGCTTCAAAGC
      D  S  V  M  M  G  A  D  T  Y  E  T  E  E  E  A  S  K
5581  TACTGTTAGCTGGGAAGTCCCAGTTGGAATAGGAAGAACACAAAGATAAGgtgagtat
      L  L  L  A  G  K  V  P  V  G  I  G  R  N  T  K  I  R
5641  ggatgtgaaccaccggttagtcccaaaatatcactcactgatactgatggtatcct
```

FIG. 1F

```
5701 ctgattatttcagGAACTGTATCATTGACACATGAATGCTAGGATTGGGAAGAACGTGGTG
              N  C  I  I  D  M  N  A  R  I  G  K  N  V  V
5761 ATCACAAACAGTAAGgtgagcgagcgacctacatgggtgcagaatccttgtgtgctccatc
      I  T  N  S  K
5821 tatcctaattcggtaattcctatccagcgctagtcttgtgaccatgggcatgggttcga
5881 ctctgtgacagGGCATCCAAGAGGCTGATCACCCGGAAGAGGGTACTACATAAGGTCTG
               G  I  Q  E  A  D  H  P  E  E  G  Y  Y  I  R  S
5941 GAATCGTGGTGATCTTGAAGAATGCAACGATCAACGATGGGTCTCTGTCATATAGATCGGCT
      G  I  V  V  I  L  K  N  A  T  I  N  D  G  S  V  I  -
6001 GCGTGTGCGTCTACAAAACAAGAACCTACAATGGTATTGCATCGATGGATCGTGTAACCT
6061 TGGTATGGTAAGAGCCGCTTGACAGAAAGTCGAGAGTTCGGGCAAGATGCGTAGTCTGGC
6121 ATGCTGTTCCTTGACCATTGTGCTAGTATGTACTGTTATAAGCTGCGCCCTAGAAGTT
6181 GCAGCAAACCTTTTTATGAACCTTTGTATTCCATTACCTGCTTTGATCAACTATATCT
6241 GTCATCCTATATATTACTAAATTTTACGTGTTTTTCTAATTCGGTGCTGCTTTTGGGAT
```

FIG. 1G

SEQUENCE LISTING

<160> NUMBER OF SEQ ID NOS: 10

<210> SEQ ID NO 1
<211> LENGTH: 33
<212> TYPE: PRT
<213> ORGANISM: HS 33 Mutant of Zea mays

<400> SEQUENCE: 1

Leu His Asp Phe Gly Ser Glu Ile Leu Pro Arg Ala Val Leu Asp Tyr
1               5                   10                  15

Ser Val Gln Ala Cys Ile Phe Thr Gly Tyr Trp Glu Asp Val Gly Thr
            20                  25                  30

Ile

<210> SEQ ID NO 2
<211> LENGTH: 20
<212> TYPE: PRT
<213> ORGANISM: RTS48-2 Mutant of Zea mays

<400> SEQUENCE: 2

Thr Gln Met Pro Glu Glu Pro Val Gly Trp Phe Gln Gly Thr Ala Asp
1               5                   10                  15

Ser Ile Arg Lys
            20

<210> SEQ ID NO 3
<211> LENGTH: 18
<212> TYPE: PRT
<213> ORGANISM: RTS60-1 Mutant of Zea mays

<400> SEQUENCE: 3

Asp Lys Cys Lys Met Lys Tyr Val Phe Ile Ser Asp Gly Cys Leu Leu
1               5                   10                  15

Arg Glu

<210> SEQ ID NO 4
<211> LENGTH: 7739
<212> TYPE: DNA
<213> ORGANISM: Wild-type Shrunken-2 allele of Zea mays

<400> SEQUENCE: 4

```
taagaggggt gcacctagca tagatttttt gggctccctg gcctctcctt tcttccgcct      60
gaaaacaacc tacatggata catctgcaac cagagggagt atctgatgct ttttcctggg     120
cagggagagc tatgagacgt atgtcctcaa agccactttg cattgtgtga accaatatc     180 gatctttgtt acttcatcat gcatgaacat ttgtggaaac tactagctta caagcattag     240
tgacagctca gaaaaagtt atctctgaaa ggtttcatgt gtaccgtggg aaatgagaaa      300
tgttgccaac tcaaacacct tcaatatgtt gtttgcaggc aaactcttct ggaagaaagg     360
tgtctaaaac tatgaacggg ttacagaaag gtataaacca cggctgtgca ttttggaagt     420
atcatctata gatgtctgtt gagggggaaag ccgtacgcca acgttattta ctcagaaaca    480
gcttcaacac acagttgtct gctttatgat ggcatctcca cccaggcacc caccatcacc     540
tattcaccta tctctcgtgc ctgtttattt tcttgcccctt tctgatcata aaaaatcatt    600
aagagtttgc aaacatgcat aggcatatca atatgctcat ttattaattt gctagcagat     660
catcttccta ctctttactt tatttattgt ttgaaaaata tgtcctgcac ctagggagct     720
```

-continued

```
cgtatacagt accaatgcat cttcattaaa tgtgaatttc agaaaggaag taggaaccta        780
tgagagtatt tttcaaaatt aattagcggc ttctattatg tttatagcaa aggccaaggg        840
caaaatcgga acactaatga tggttggttg catgagtctg tcgattactt gcaagaaatg        900
tgaacctttg tttctgtgcg tgggcataaa acaaacagct tctagcctct tttacggtac        960
ttgcacttgc aagaaatgtg aactcctttt catttctgta tgtggacata atgccaaagc       1020
atccaggctt tttcatggtt gttgatgtct ttacacagtt catctccacc agtatgccct       1080
cctcatactc tatataaaca catcaacagc atcgcaatta gccacaagat cacttcggga       1140
ggcaagtgtg atttcgacct tgcagccacc ttttttttgtt ctgttgtaag tatactttcc      1200
cttaccatct ttatctgtta gtttaatttg taattgggaa gtattagtgg aaagaggatg       1260
agatgctatc atctatgtac tctgcaaatg catctgacgt tatatgggct gcttcatata       1320
atttgaattg ctccattctt gccgacaata tattgcaagg tatatgccta gttccatcaa       1380
aagttctgtt ttttcattct aaaagcattt tagtggcacg caattttgtc catgagggaa       1440
aggaaatctg ttttggttac tttgcttgag gtgcattctt catatgtcca gttttatgga       1500
agtaataaac ttcagtttgg tcataagatg tcatattaaa gggcaaacat atattcaatg       1560
ttcaattcat cgtaaatgtt ccctttttgt aaaagattgc atactcattt atttgagttg       1620
caggtgtatc tagtagttgg aggagatatg cagtttgcac ttgcattgga cacgaactca       1680
ggtcctcacc agataagatc ttgtgagggt gatgggattg acaggttgga aaaattaagt       1740
attgggggca gaaagcagga gaaagctttg agaaataggt gctttggtgg tagagttgct       1800
gcaactacac aatgtattct tacctcagat gcttgtcctg aaactcttgt aagtatccac       1860
ctcaattatt actcttacat gttggtttac tttacgtttg tcttttcaag ggaaaatttac      1920 tgtattttttt gtgttttgtg ggagttctat acttctgttg gactggttat tgtaaagatt     1980
tgttcaaata gggtcatcta ataattgttt gaaatctggg aactgtggtt tcactgcgtt       2040
caggaaaaag tgaattattg gttactgcat gaataactta tggaaataga ccttagagtt       2100
gctgcatgat tatcacaaat cattgctacg atatcttata atagttcttt cgacctcgca       2160
ttacatatat aactgcaact cctagttgcg ttcaaaaaaa aaaatgcaac tcttagaacg       2220
ctcaccagtg taatctttcc tgaattgtta tttaatggca tgtatgcact acttgtatac       2280
ttatctagga ttaagtaatc taactctagg ccccatattt gcagcattct caaacacagt       2340
cctctaggaa aaattatgct gatgcaaacc gtgtatctgc tatcattttg ggcggaggca       2400
ctggatctca gctctttcct ctgacaagca caagagctac gcctgctgta agggataaca       2460
ctgaacatcc aacgttgatt actctattat agtattatac agactgtact tttcgaattt       2520
atcttagttt tctacaatat ttagtggatt cttctcattt tcaagataca caattgatcc       2580
ataatcgaag tggtatgtaa gacagtgagt taaaagatta tattttttgg gagacttcca      2640
gtcaaatttt cttagaagtt tttttggtcc agatgttcat aaagtcgccg ctttcatact       2700 tttttttaatt ttttaattgg tgcactatta ggtacctgtt ggaggatgtt acaggcttat      2760
tgatatccct atgagtaact gcttcaacag tggtataaat aagatatttg tgatgagtca       2820
gttcaattct acttcgctta accgccatat tcatcgtaca taccttgaag gcgggatcaa       2880 cttttgctgat ggatcgtac aggtgattta cctcatcttg ttgatgtgta atactgtaat       2940
taggagtaga tttgtgtgga gagaataata aacagatgcc gagattcttt tctaaaagtc       3000
tagatccaaa ggcattgtgg ttcaaaacac tatggacttc taccatttat gtcattactt       3060
tgccttaatg ttccattgaa tggggcaaat tattgattct acaagtgttt aattaaaaac       3120
```

-continued

```
taattgttca tcctgcaggt attagcggct acacaaatgc ctgaagagcc agctggatgg    3180
ttccagggta cagcagactc tatcagaaaa tttatctggg tactcgaggt agttgatatt    3240
ttctcgttta tgaatgtcca ttcactcatt cctgtagcat tgtttctttg taattttgag    3300
ttctcctgta tttctttagg attattacag tcacaaatcc attgacaaca ttgtaatctt    3360
gagtggcgat cagctttatc ggatgaatta catggaactt gtgcaggtat ggtgttctct    3420
tgttcctcat gtttcacgta atgtcctgat tttggattaa ccaactactt ttggcatgca    3480
ttatttccag aaacatgtcg aggacgatgc tgatatcact atatcatgtg ctcctgttga    3540
tgagaggtaa tcagttgttt atatcatcct aatatgaata tgtcatcttg ttatccaaca    3600
caggatgcat atggtctaat ctgctttcct ttttttccc ttcggaagcc gagcttctaa    3660
aaatgggcta gtgaagattg atcatactgg acgtgtactt caattctttg aaaaaccaaa    3720
gggtgctgat ttgaattcta tggttagaaa ttccttgtgt aatccaattc ttttgttttc    3780 cttctttct tgagatgaac ccctctttta gttatttcca tggataaccct gtacttgact    3840 tattcagaaa tgattttcta ttttgctgta gaatctgaca ctaaagctaa tagcactgat    3900
gttgcagaga gttgagacca acttcctgag ctatgctata gatgatgcac agaaatatcc    3960
ataccttgca tcaatgggca tttatgtctt caagaaagat gcacttttag accttctcaa    4020
gtaatcactt tcctgtgact tatttctatc caactcctag tttaccttct aacagtgtca    4080
attcttaggt caaatatac tcaattacat gactttggat ctgaaatcct cccaagagct    4140
gtactagatc atagtgtgca ggtaagtctg atctgtctgg agtatgtgtt ctgtaaactg    4200
taaattcttc atgtcaaaaa gttgttttg tttccagttt ccactaccaa tgcacgattt    4260
atgtattttc gcttccatgc atcatacata ctaacaatac attttacgta ttgtgttagg    4320
catgcatttt tacgggctat tgggaggatg ttggaacaat caaatcattc tttgatgcaa    4380
acttggccct cactgagcag gtactctgtc atgtattctg tactgcatat atattacctg    4440
gaattcaatg catagaatgt gttagaccat cttagttcca tcctgttttc ttcaattagc    4500
ttatcattta atagttgttg gctagaattt aaacacaaat ttacctaata tgtttctctc    4560
ttcagccttc caagtttgat ttttacgatc caaaacacc tttcttcact gcaccccgat    4620
gcttgcctcc gacgcaattg gacaagtgca aggtatatgt cttactgagc acaattgtta    4680
cctgagcaag attttgtgta cttgacttgt tctcctccac agatgaaata tgcatttatc    4740
tcagatggtt gcttactgag agaatgcaac atcgagcatt ctgtgattgg agtctgctca    4800
cgtgtcagct ctggatgtga actcaaggta catactctgc caatgtatct actcttgagt    4860
ataccatttc aacaccaagc atcaccaaat cacacagaac aatagcaaca aagccttta    4920 gttccaagca atttagggta gcctagagtt gaaatctaac aaaacaaaag tcaaagctct    4980
atcacgtgga tagttgtttt ccatgcactc ttatttaagc taattttttg ggtatactac    5040
atccatttaa ttattgtttt attgcttctt ccctttgcct ttcccccatt actatcgcgt    5100
cttaagatca tactacgcac tagtgtcttt agaggtctct ggtggacatg ttcaaaccat    5160
ctcaatcggt gttggacaag ttttttcttga atttgtgcta cacctaacct atcacgtatg    5220
tcatcgtttc aaactcgatc cttcctgtat catcataaat ccaatgcaac atacgcattt    5280
atgcaacatt tatctgttga acatgtcatc ttttgtagg ttaacattat gcaccataca    5340
atgtagcatg tctaatcatc atcctataaa atttacattt tagcttatgt ggtatccctct    5400 tgccacttag aacaccatat gcttgatgcc atttcatcca ccctgctttg attctatggc    5460
```

-continued

```
taacatcttc attaatatcc tcgcctctct gtatcattgg tcctaaatat ggaaatacat      5520
tctttctggg cactacttga ccttccaaac taacgtctcc tttgctcctt tcttgtgtgt      5580
agtagtaccg aagtcacatc tcatatattc ggttttagtt ctactaagtc ccggttcga       5640 tcccctcag gggtgaattt cgggcttggt aaaaaaaatc ccctcgctgt gtcccgcccg       5700
ctctcgggga tcgatatcct gcgcgccacc ctccggctgg gcattgcaga gtgagcagtt      5760
gatcggctcg ttagtgatgg ggagcggggt tcaagggttt tctcggccgg gaccatgttt      5820
cggtctctta atataatgcc gggagggcag tctttccctc cccggtcgag ttttagttct      5880
accgagtcta aaacctttgg actctagagt cccctgtcac aactcacaac tctagttttc      5940
tatttacttc tacctagcgt ttattaatga tcactatatc gtctgtaaaa agcatacacc      6000
aatgtaatcc ccttgtatgt cccttgtaat attatccatc acaagaaaaa aaggtaaggc      6060
tcaaagttga cttttgatat agtcctattc taatcgagaa gtcatctgta tcttcgtctc      6120
ttgttcgaac actagtcaca aaattttttg tacatgttct taatgagtcc aacgtaatat      6180
tccttgatat tttgtcataa gccctcatca agtcaatgaa aatcacgtgt aggtccttca      6240
tttgttcctt atactgctcc atcacttgtc tcattaagaa aatctctctc atagttaacc      6300
ttttggcatg aaacaaaatc acacagaagt tgtttccttt ttttaagatc ccacacaaaa      6360
gaggtttgat ctaaggaatc tggatccctg acaggtttat caaaatcctt tgtgtttttc      6420
ttaaaactga atattcctcc agcttctagt attgatgtaa tattcaatct gtttagcaag      6480
tgaacacctt ggttcttgtt gttactgtac ccccccccccc cccccccccc cgaggcccag     6540
attaccacga catgaataca agaatattga acccagatct agagtttgtt tgtactgttg      6600
aaaatcggtg acaattcatt ttgttattgc gctttctgat aacgacagga ctccgtgatg      6660
atgggagcgg acacctatga aactgaagaa gaagcttcaa agctactgtt agctgggaag      6720
gtcccagttg aataggaag gaacacaaag ataaggtgag tatggatgtg gaaccaccgg       6780
ttagttccca aaaatatcac tcactgatac ctgatggtat cctctgatta ttttcaggaa      6840
ctgtatcatt gacatgaatg ctaggattgg gaagaacgtg gtgatcacaa acagtaaggt      6900
gagcgagcgc acctacatgg gtgcagaatc ttgtgtgctc atctatccta attcggtaat      6960
tcctatccag cgctagtctt gtgaccatgg ggcatgggtt cgactctgtg acagggcatc      7020
caagaggctg atcacccgga agaagggtac tacataaggt ctggaatcgt ggtgatcttg      7080
aagaatgcaa ccatcaacga tgggtctgtc atatagatcg gctgcgtgtg cgtctacaaa      7140
acaagaacct acaatggtat tgcatcgatg gatcgtgtaa ccttggtatg gtaagagccg      7200
cttgacagaa agtcgagcgt tcgggcaaga tgcgtagtct ggcatgctgt tccttgacca      7260
tttgtgctgc tagtatgtac tgttataagc tgccctagaa gttgcagcaa acctttttat      7320
gaacctttgt atttccatta cctgctttgg atcaactata tctgtcatcc tatatattac      7380
taaattttta cgtgttttttc taattcggtg ctgcttttgg gatctggctt cgatgaccgc      7440
tcgaccctgg gccattggtt cagctctgtt ccttagagca actccaagga gtcctaaatt      7500
ttgtattaga tacgaaggac ttcagccgtg tatgtcgtcc tcaccaaacg ctcttttttgc     7560 atagtgcagg ggttgtagac ttgtagccct tgtttaaaga ggaatttgaa tatcaaatta      7620
taagtattaa atatatattt aattaggtta acaaatttgg ctcgttttta gtctttattt      7680
atgtaattag ttttaaaaat agacctatat ttcaatacga aatatcatta acatcgata       7739
```

<210> SEQ ID NO 5
<211> LENGTH: 20

```
<212> TYPE: DNA
<213> ORGANISM: Artificial sequence
<220> FEATURE:
<223> OTHER INFORMATION: Synthetic oligonucleotide primer

<400> SEQUENCE: 5
cgactcacta tagggagacc                                              20

<210> SEQ ID NO 6
<211> LENGTH: 15
<212> TYPE: DNA
<213> ORGANISM: Artificial Sequence
<220> FEATURE:
<223> OTHER INFORMATION: Synthetic oligonucleotide primer

<400> SEQUENCE: 6
ccctatgagt aactg                                                   15

<210> SEQ ID NO 7
<211> LENGTH: 15
<212> TYPE: DNA
<213> ORGANISM: Artificial Sequence
<220> FEATURE:
<223> OTHER INFORMATION: Synthetic oligonucleotide primer

<400> SEQUENCE: 7
tatactcaat tacat                                                   15

<210> SEQ ID NO 8
<211> LENGTH: 19
<212> TYPE: DNA
<213> ORGANISM: Artificial Sequence
<220> FEATURE:
<223> OTHER INFORMATION: Synthetic oligonucleotide primer

<400> SEQUENCE: 8
gtgccacctg acgtctaag                                               19

<210> SEQ ID NO 9
<211> LENGTH: 15
<212> TYPE: DNA
<213> ORGANISM: Artificial Sequence
<220> FEATURE:
<223> OTHER INFORMATION: Synthetic oligonucleotide primer

<400> SEQUENCE: 9
cagagctgac acgtg                                                   15

<210> SEQ ID NO 10
<211> LENGTH: 16
<212> TYPE: DNA
<213> ORGANISM: Artificial Sequence
<220> FEATURE:
<223> OTHER INFORMATION: Synthetic oligonucleotide primer

<400> SEQUENCE: 10
aagctgatcg ccactc                                                  16
```

HEAT STABLE MUTANTS OF STARCH BIOSYNTHESIS ENZYMES

CROSS-REFERENCE TO RELATED APPLICATION

This application claims the benefit of U.S. Provisional application Ser. No. 60/275,768, filed Mar. 14, 2001.

This invention was made with government support under National Science Foundation grant number 9316887. The government has certain rights in the invention.

BACKGROUND OF THE INVENTION

The sessile nature of plant life generates a constant exposure to environmental factors that exert positive and negative effects on its growth and development. One of the major impediments facing modem agriculture is adverse environmental conditions. One important factor which causes significant crop loss is heat stress. Temperature stress greatly reduces grain yield in many cereal crops such as maize, wheat, and barley. Yield decreases due to heat stress range from 7 to 35% in the cereals of world-wide importance.

A number of studies have identified likely physiological consequences of heat stress. Early work by Hunter et al. (Hunter, R. B., Tollenaar, M., and Breuer, C. M. [1977] *Can. J. Plant Sci.* 57:1127–1133) using growth chamber conditions showed that temperature decreased the duration of grain filling in maize. Similar results in which the duration of grain filling was adversely altered by increased temperatures were identified by Tollenaar and Bruulsema (Tollenaar, M. and Bruulsema, T. W. [1988] *Can. J. Plant Sci.* 68:935–940). Badu-Apraku et al. (Badu-Apraku, B., Hunter, R. B., and Tollenaar, M. [1983] *Can. J. Plant. Sci.* 63:357–363) measured a marked reduction in the yield of maize plants grown under the day/night temperature regime of 35/15° C. compared to growth in a 25/15° C. temperature regime. Reduced yields due to increased temperatures is also supported by historical as well as climatological studies (Thompson, L. M. [1986]*Agron. J.* 78:649–653; Thompson, L. M. [1975] *Science* 188:535–541; Chang, J. [1981] *Agricul. Metero.* 24:253–262; and Conroy, J. P., Seneweera, S., Basra, A. S., Rogers, G., and Nissen-Wooller, B. [1994] *Aust. J. Plant Physiol.* 21:741–758).

That the physiological processes of the developing seed are adversely affected by heat stress is evident from studies using an in vitro kernel culture system (Jones, R. J. Grengenbach, B. G., and Cardwell, V. B. [1981] *Crop Science* 21:761–766; Jones, R. J., Ouattar, S., and Crookston, R. K. [1984] *Crop Science* 24:133–137; and Cheikh, N., and Jones, R. J. [1995 ] *Physol. Plant.* 59–66). Maize kernels cultured at the above-optimum temperature of35° C. exhibited a dramatic reduction in weight.

Work with wheat identified the loss of soluble starch synthase (SSS) activity as a hallmark of the wheat endosperm's response to heat stress (Hawker, J. S. and Jenner, C. F. [1993] *Aust. J. Plant Physiol.* 20:197–209; Denyer, K., Hylton, C. M., and Smith, A. M. [1994]*Aust. J. Plant Physiol.* 21:783–789; Jenner, C. F. [1994] *Aust. J. Plant Physiol.* 21:791–806). Additional studies with SSS of wheat endosperm show that it is heat labile (Rijven, A. H. G. C. [1986]*Plant Physiol.* 81:448–453; Keeling, P. L., Bacon, P. J., Holt, D. C. [1993]*Planta.* 191:342–348; Jenner, C. F., Denyer, K., and Guerin, J. [1995] *Aust. J. Plant Physiol.* 22:703–709).

The roles of SSS and ADP glucose pyrophosphorylase (AGP) under heat stress conditions in maize is less clear. AGP catalyzes the conversion of ATP and α-glucose-1-phosphate to ADP-glucose and pyrophosphate. ADP-glucose is used as a glycosyl donor in starch biosynthesis by plants and in glycogen biosynthesis by bacteria. The importance of ADP-glucose pyrophosphorylase as a key enzyme in the regulation of starch biosynthesis was noted in the study of starch deficient mutants of maize (*Zea mays*) endosperm (Tsai, C. Y., and Nelson, Jr., O. E. [1966] *Science* 151:341–343; Dickinson, D. B., J. Preiss [1969] *Plant Physiol.* 44:1058–1062).

Ou-Lee and Setter (Ou-Lee, T. and Setter, T.L. [1985] *Plant Physiol.* 79:852–855) examined the effects of temperature on the apical or tip regions of maize ears. With elevated temperatures, AGP activity was lower in apical kernels when compared to basal kernels during the time of intense starch deposition. In contrast, in kernels developed at normal temperatures, AGP activity was similar in apical and basal kernels during this period. However, starch synthase activity during this period was not differentially affected in apical and basal kernels. Further, heat-treated apical kernels exhibited an increase in starch synthase activity over control. This was not observed with AGP activity. Singletary et al. (Singletary, G. W., Banisadr, R., and Keeling, P. L. [1993] *Plant Physiol.* 102: 6 (suppl).; Singletary, G. W., Banisadra, R., Keeling, P. L. [1994]*Aust. J. Plant Physiol.* 21:829–841) using an in vitro culture system quantified the effect of various temperatures during the grain fill period. Seed weight decreased steadily as temperature increased from 22–36° C. A role for AGP in yield loss is also supported by work from Duke and Doehlert (Duke, E. R. and Doehlert, D. C. [1996] *Environ. Exp. Botany.* 36:199–208).

Work by Keeling et al. (1994, supra) quantified SSS activity in maize and wheat using $Q_{10}$ analysis, and showed that SSS is an important control point in the flux of carbon into starch.

In vitro biochemical studies with AGP and SSS clearly show that both enzymes are heat labile. Maize endosperm AGP loses 96% of its activity when heated at 57° C. for five minutes (Hannah, L. C., Tuschall, D. M., and Mans, R. J. [1980] *Genetics* 95:961–970). This is in contrast to potato AGP which is fully stable at 70° C. (Sowokinos, J. R. and Preiss, J. [1982]*Plant Physiol.* 69:1459–1466; Okita, T. W., Nakata, P. A., Anderson, J. M., Sowokinos, J., Morell, J., and Preiss, J. [1990] *Plant Physiol.* 93:785–90). Heat inactivation studies with SSS showed that it is also labile at higher temperatures, and kinetic studies determined that the Km value for amylopectin rose exponentially when temperature increased from 25–45° C. (Jenner et al., 1995, supra).

Biochemical and genetic evidence has identified AGP as a key enzyme in starch biosynthesis in higher plants and glycogen biosynthesis in *E. coli* (Preiss, J. and Romeo, T. [1994] *Progress in Nuc. Acid Res. and Mol Biol.* 47:299–329; Preiss, J. and Sivak, M. [1996] "Starch synthesis in sinks and sources," *In Photoassimilate distribution in plants and crops: source-sink relationships.* Zamski, E., ed., Marcil Dekker Inc. pp. 139–168). AGP catalyzes what is viewed as the initial step in the starch biosynthetic pathway with the product of the reaction being the activated glucosyl donor, ADPglucose. This is utilized by starch synthase for extension of the polysaccharide polymer (reviewed in Hannah, L. Curtis [1996] "Starch synthesis in the maize endosperm," In: *Advances in Cellular and Molecular Biology of Plants,* Vol. 4. B. A. Larkins and I. K. Vasil (eds.). Cellular and Molecular Biology of Plant Seed Development. Kluwer Academic Publishers, Dordrecht, The Netherlands).

Initial studies with potato AGP showed that expression in *E. coli* yielded an enzyme with allosteric and kinetic properties very similar to the native tuber enzyme (Iglesias, A., Barry, G. F., Meyer, C., Bloksberg, L., Nakata, P., Greene, T., Laughlin, M. J., Okita, T. W., Kishore, G. M., and Preiss, J. [1993] *J. Biol Chem.* 268:1081–86; Ballicora, M. A., Laughlin, M. J., Fu, Y., Okita, T. W., Barry, G. F., and Preiss, J. [1995] *Plant Physiol.* 109:245–251). Greene et al. (Greene, T. W., Chantler, S. E., Kahn, M. L., Barry, G. F., Preiss, J., and Okita, T. W. [1996] *Proc. Natl. Acad. Sci.* 93:1509–1513; Greene, T. W., Woodbury, R. L., and Okita, T. W. [1996] *Plant Physiol.* (112:1315–1320) showed the usefulness of the bacterial expression system in their structure-function studies with the potato AGP. Multiple mutations important in mapping allosteric and substrate binding sites were identified (Okita, T. W., Greene, T. W., Laughlin, M. J., Salamone, P., Woodbury, R., Choi, S., Ito, H., Kavakli, H., and Stephens, K. [1996] "Engineering Plant Starches by the Generation of Modified Plant Biosynthetic Enzymes," In *Engineering Crops for Industrial End Uses*, Shewry, P. R., Napier, J. A., and Davis, P., eds., Portland Press Ltd., London).

AGP enzymes have been isolated from both bacteria and plants. Bacterial AGP consists of a homotetramer, while plant AGP from photosynthetic and non-photosynthetic tissues is a heterotetramer composed of two different subunits. The plant enzyme is encoded by two different genes, with one subunit being larger than the other. This feature has been noted in a number of plants. The AGP subunits in spinach leaf have molecular weights of 54 kDa and 51 kDa, as estimated by SDS-PAGE. Both subunits are immunoreactive with antibody raised against purified AGP from spinach leaves (Copeland, L., J. Preiss (1981) *Plant Physiol.* 68:996–1001; Morell, M., M. Bloon, V. Knowles, J. Preiss [1988] *J. Bio. Chem.* 263:633). Immunological analysis using antiserum prepared against the small and large subunits of spinach leaf showed that potato tuber AGP is also encoded by two genes (Okita et al., 1990, supra). The cDNA clones of the two subunits of potato tuber (50 and 51 kDa) have also been isolated and sequenced (Muller-Rober, B. T., J. Kossmann, L. C. Hannah, L. Willmitzer, U. Sounewald [1990] *Mol. Gen. Genet.* 224:136–146; Nakata, P. A., T. W. Greene, J. M. Anderson, B. J. Smith-White, T. W. Okita, J. Preiss [1991] *Plant Mol. Biol.* 17:1089–1093). The large subunit of potato tuber AGP is heat stable (Nakata et al. [1991], supra).

As Hannah and Nelson (Hannah, L. C., O. E. Nelson (1975) *Plant Physiol.* 55:297-302.; Hannah, L. C., and Nelson, Jr., O. E. [1976] *Biochem. Genet.* 14:547–560) postulated, both Shrunken-2 (Sh2) (Bhave, M. R., S. Lawrence, C. Barton, L. C. Hannah [1990] *Plant Cell* 2:581–588) and Brittle-2 (Bt2) (Bae, J. M., M. Giroux, L. C. Hannah [1990] *Maydica* 35:317–322) are structural genes of maize endosperm ADP-glucose pyrophosphorylase. Sh2 and Bt2 encode the large subunit and small subunit of the enzyme, respectively. From cDNA sequencing, Sh2 and Bt2 proteins have predicted molecular weight of 57,179 Da (Shaw, J. R., L. C. Hannah [1992] *Plant Physiol.* 98:1214–1216) and 52,224 Da, respectively. The endosperm is the site of most starch deposition during kernel development in maize. Sh2 and bt2 maize endosperm mutants have greatly reduced starch levels corresponding to deficient levels of AGP activity. Mutations of either gene have been shown to reduce AGP activity by about 95% (Tsai and Nelson, 1966, supra; Dickinson and Preiss, 1969, supra). Furthermore, it has been observed that enzymatic activities increase with the dosage of functional wild type Sh2 and Bt2 alleles, whereas mutant enzymes have altered kinetic properties. AGP is the rate limiting step in starch biosynthesis in plants. Stark et al. placed a mutant form of *E. coli* AGP in potato tuber and obtained a 35% increase in starch content (Stark et al. [1992] *Science* 258:287).

The cloning and characterization of the genes encoding the AGP enzyme subunits have been reported for various plants. These include Sh2 cDNA (Bhave et al., 1990, supra), Sh2 genomic DNA (Shaw and Hannah, 1992, supra), and Bt2 cDNA (Bae et al., 1990, supra) from maize; small subunit cDNA (Anderson, J. M., J. Hnilo, R. Larson, T. W. Okita, M. Morell, J. Preiss [1989] *J. Biol. Chem.* 264:12238–12242) and genomic DNA (Anderson, J. M., R. Larson, D. Landencia, W. T. Kim, D. Morrow, T. W. Okita, J. Preiss [1991] *Gene* 97:199–205) from rice; and small and large subunit cDNAs from spinach leaf (Morell et al., 1988, supra) and potato tuber (Muller-Rober et al., 1990, supra; Nakata, P. A., Greene, T. W., Anderson, J. W., Smith-White, B. J., Okita, T. W., and Preiss, J. [1991] *Plant Mol. Biol.* 17:1089–1093). In addition, cDNA clones have been isolated from wheat endosperm and leaf tissue (Olive, M. R., R. J. Ellis, W. W. Schuch [1989] *Plant Physiol. Mol. Biol.* 12:525–538) and *Arabidopsis thaliana* leaf (Lin, T., Caspar, T., Sommerville, C. R., and Preiss, J. [1988] *Plant Physiol.* 88:1175–1181). AGP sequences from barley have also been described in Ainsworth et al. (Ainsworth, C., Hosein, F., Tarvis, M., Weir, F., Burrell, M., Devos, K. M., Gale, M. D. [1995] *Planta* 197:1–10).

AGP functions as an allosteric enzyme in all tissues and organisms investigated to date. The allosteric properties of AGP were first shown to be important in *E. coli*. A glycogen-overproducing *E. coli* mutant was isolated and the mutation mapped to the structural gene for AGP, designated as glyc. The mutant *E. coli*, known as glyc-16, was shown to be more sensitive to the activator, fructose 1,6 bisphosphate, and less sensitive to the inhibitor, cAMP (Preiss, J. [1984] *Ann. Rev. Microbiol.* 419–458). Although plant AGP's are also allosteric, they respond to different effector molecules than bacterial AGP'S. In plants, 3-phosphoglyceric acid (3-PGA) functions as an activator while phosphate ($PO_4$) serves as an inhibitor (Dickinson and Preiss, 1969, supra).

Using an in vivo mutagenesis system created by the Ac-mediated excision of a Ds transposable element fortuitously located close to a known activator binding site, Giroux et al. (Giroux, M. J., Shaw, J., Barry, G., Cobb, G. B., Greene, T., Okita, T. W., and Hannah, L. C. [1996] *Proc. Natl. Acad. Sci.* 93:5824–5829) were able to generate site-specific mutants in a functionally important region of maize endosperm AGP. One mutant, Rev6, contained a tyrosine-serine insert in the large subunit of AGP and conditioned a 11–18% increase in seed weight. In addition, published international application WO 01/64928 teaches that various characteristics, such as seed number, plant biomass, Harvest Index etc., can be increased in plants transformed with a polynucleotide encoding a large subunit of maize AGP containing the Rev6 mutation.

Published international patent applications WO 99/58698 and WO 98/22601 and issued U.S. Pat. No. 6,069,300 disclose mutations in the large subunit of maize AGP enzyme that, when expressed, confers increased heat stability in comparison to that observed for wild type AGP enzyme. Several heat stable mutants are disclosed in the '300 patent and WO publications, including mutants designated as HS 13 (having an Ala to Pro substitution at position 177); HS 14 (having an Asp to His substitution at position 400 and a Val to Ile substitution at position 454; HS 16 (having an Arg to Thr substitution at position 104); HS 33 (having a His to Tyr substitution at position 333); HS 39 (having a His to Tyr substitution at position 333); HS 40

(having a His to Tyr substitution at position 333 and a Thr to Ile substitution at position 460); HS 47 (having an Arg to Pro substitution at position 216 and a His to Tyr substitution at position 333); RTS 48-2 (having an Ala to Val substitution at position 177); and RTS 60-1 (having an Ala to Val substitution at position 396).

BRIEF SUMMARY OF THE INVENTION

The subject invention pertains to materials and methods useful for improving crop yields in plants, such as those plants that produce cereal crops. In one embodiment, the subject invention provides heat stable AGP enzymes and nucleotide sequences which encode these enzymes. In a preferred embodiment, the heat stable enzymes of the invention can be used to provide plants having greater tolerance to higher temperatures, thus enhancing the crop yields from these plants. In a particularly preferred embodiment, the improved plant is a cereal. Cereals to which this invention applies include, for example, maize, wheat, rice, and barley.

BRIEF DESCRIPTION OF THE DRAWINGS

FIGS. 1A–1G show the genomic nucleotide sequence of a wild type Shrunken-2 allele of *Zea mays*. Introns are indicated by lower case letters. Base number 1 is the transcription start site.

"sh2"=wild type sh2 protein;
"sh2ht"=wild type sh2 protein, following heat treatment;
"33"=sh2 protein containing the HS 33 mutation (i.e., a histidine-to-tyrosine amino acid substitution at position 333 in the large subunit of maize AGP);
"33ht"=sh2 protein containing the HS 33 mutation, following heat treatment;
"177"=sh2 protein containing the mutation rts48-2 (i.e., an alanine-to-valine amino acid substitution at position 177 in the large subunit of maize AGP);
"177ht"=sh2 protein containing the mutation rts48-2 (i.e., an alanine-to-valine amino acid substitution at position 177 in the large subunit of maize AGP), following heat treatment;
"396"=sh2 protein containing the mutation rts60-1 (i.e., an alanine-to-valine amino acid substitution at position 396 in the large subunit of maize AGP);
"396ht"=sh2 protein containing the mutation rts60-1 (i.e., an alanine-to-valine amino acid substitution at position 396 in the large subunit of maize AGP), following heat treatment;
"7+6"=sh2 protein containing the combination of "177" and "396" mutations;
"7+6ht"=sh2 protein containing the combination of "177" and "396" mutations, following heat treatment;
"7+3"=sh2 protein containing the combination of "177" and "HS 33" mutations;
"7+3ht"=sh2 protein containing the combination of "177" and "HS 33" mutations, following heat treatment;
"6+3"=sh2 protein containing the combination of "396" and "HS 33" mutations;
"6+3ht"=sh2 protein containing the combination of "396" and "HS 33" mutations, following heat treatment.

Figure 3:
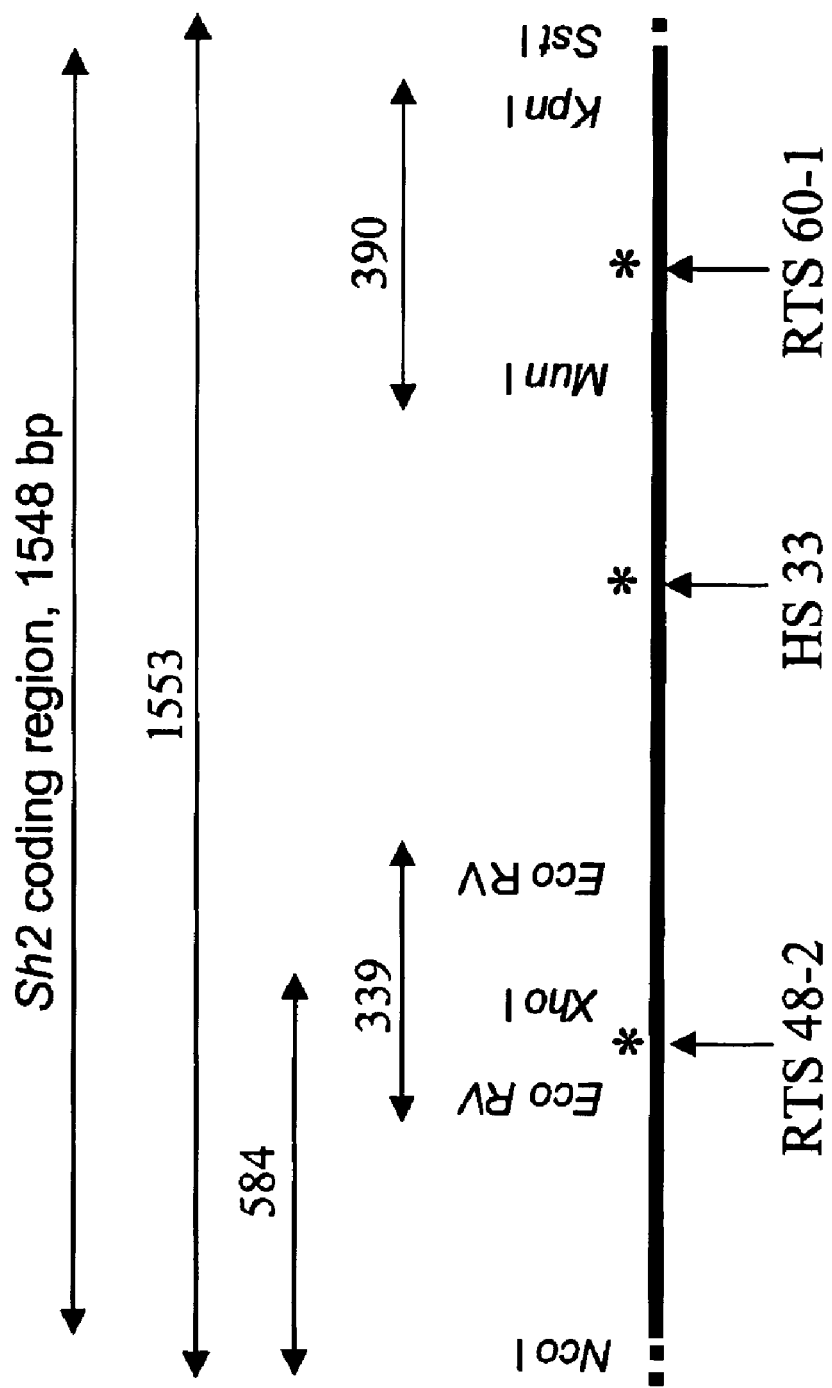

FIG. 3 shows a restriction map of Sh2 coding region. Restriction enzymes shown are those used in isolation of entire coding region and in creation of double and triple mutants. Mutations are indicated with asterisks (*)

BRIEF DESCRIPTION OF THE SEQUENCES

SEQ ID NO. 1 is an amino acid sequence of a region corresponding to amino acids 318 to 350 of the large subunit of AGP in maize containing the HS 33 mutation.

SEQ ID NO. 2 is an amino acid sequence of a region corresponding to amino acids 170 to 189 of the large subunit of AGP in maize containing the RTS48-2 mutation.

SEQ ID NO. 3 is an amino acid sequence of a region corresponding to amino acids 389 to 406 of the large subunit of AGP in maize containing the RTS60-1 mutation.

SEQ ID NO. 4 is the genomic nucleotide sequence of a wild type Shrunken-2 allele of *Zea mays*.

SEQ ID NO. 5 is a synthetic oligonucleotide primer that can be used in accordance with the subject invention.

SEQ ID NO. 6 is a synthetic oligonucleotide primer that can be used in accordance with the subject invention.

SEQ ID NO. 7 is a synthetic oligonucleotide primer that can be used in accordance with the subject invention.

SEQ ID NO. 8 is a synthetic oligonucleotide primer that can be used in accordance with the subject invention.

SEQ ID NO. 9 is a synthetic oligonucleotide primer that can be used in accordance with the subject invention.

SEQ ID NO. 10 is a synthetic oligonucleotide primer that can be used in accordance with the subject invention.

DETAILED DISCLOSURE OF THE INVENTION

The subject invention concerns novel mutant polynucleotide molecules, and the polypeptides encoded thereby, that confer increased heat resistance and yield in plants grown under conditions of heat stress relative to plants expressing wild type genotype. In specific embodiments, the polynucleotide molecules of the subject invention encode maize endosperm ADP glucose pyrophosphorylase (AGP) and soluble starch synthase (SSS) enzyme activities.

The mutant enzymes confer increased stability to heat stress conditions during seed and plant development in seeds and plant tissue expressing the enzymes as compared with wild type enzyme activities. One aspect of the subject invention concerns polynucleotides which encode two or more amino acid changes in an AGP large subunit as compared to the wild type sequence of the AGP large subunit polypeptide, wherein the expressed mutant protein exhibits increased stability. Preferably, the polypeptide encoded by the subject polynucleotides, when expressed with the small subunit, exhibit increased enzymatic activity as compared to wild type protein and, preferably, at a level about the same or greater than that exhibited by a single amino acid mutation that confers increased heat stability, such as HS 33. The polynucleotides of the invention may encode two, three, or more amino acid changes from the wild type sequence. Preferably, a polynucleotide of the invention encodes a polypeptide having an amino acid substitution at one or more of the following positions corresponding to the position in the large subunit of maize AGP: position 177, 333, and 396.

In one embodiment, a polynucleotide of the present invention encodes a mutant large subunit of a plant AGP containing a double mutation: a histidine-to-tyrosine amino acid substitution and an alanine-to-valine amino acid substitution in the sequence of the polypeptide. In an exemplified embodiment, the histidine to tyrosine substitution occurs at the amino acid corresponding to residue number 333 in the sequence of the large subunit of maize AGP. In one embodiment, the alanine-to-valine substitution occurs at the amino acid corresponding to residue number 177 in the sequence of the large subunit of maize AGP. In another embodiment, the alanine-to-valine substitution occurs at the amino acid corresponding to residue 396 in the sequence of the large subunit of maize AGP.

Figure 2:
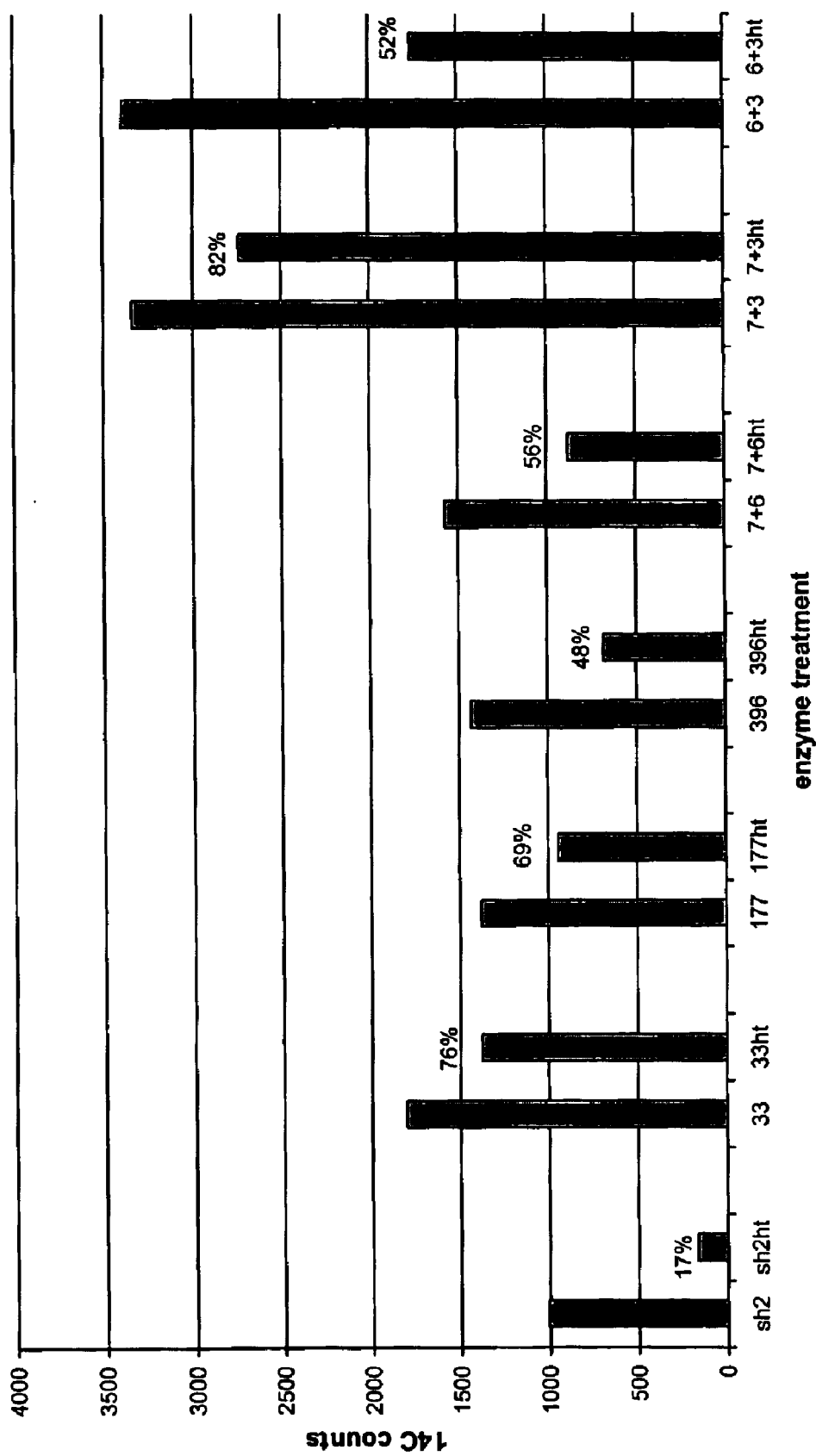
FIG. 2 shows a comparison of enzyme activity for wild type and various maize AGP large subunit mutants. All reactions were performed in duplicate. Numbers given are the average of the duplicates, after background removal. The percentages refer to activity remaining after heat treatment as compared to activity prior to heat treatment. The legend for the figure is as follows.

In a further embodiment, a polynucleotide of the present invention encodes a mutant large subunit of a plant AGP containing two alanine-to-valine amino acid substitutions within the sequence of the polypeptide. In an exemplified embodiment, the first alanine-to-valine substitution occurs at the amino acid corresponding to residue number 177 and the second alanine-to-valine substitution occurs at the amino acid corresponding to residue number 396 in the sequence of the large subunit of maize AGP. Enzyme activity associated with mutant proteins of the present invention having two mutations are shown in FIG. 2.

Another embodiment concerns a triple mutant comprising a histidine to tyrosine substitution at the amino acid corresponding to residue number 333, an alanine-to-valine substitution at the amino acid corresponding to residue number 177, and an alanine-to-valine substitution at the amino acid corresponding to residue 396 in the sequence of the large subunit of maize AGP.

The amino acid residue numbers referred to above are based on the accepted number of the amino acids in this protein (Shaw and Hannah, 1992, supra). The position of these substitutions can be readily identified by a person skilled in the art. Table 1 below shows the double and triple amino acid substitution mutants exemplified herein.

TABLE 1

| Sh2 Polypeptide Mutant | Amino Acid Change |
| --- | --- |
| HS 7 + 3 | Ala to Val at position 177 and His to Tyr at position 333 |
| HS 6 + 3 | Ala to Val at position 396 and His to Tyr at position 333 |
| HS 7 + 6 | Ala to Val at position 177 and Ala to Val at position 396 |
| HS 7 + 6 + 3 | Ala to Val at position 177 and Ala to Val at position 396 and His to Tyr at position 333 |

Because of the homology of AGP polypeptides between various species of plants (Smith-White and Preiss [1992] *J. Mol. Evol.* 34:449–464), the ordinarily skilled artisan can readily determine the position of the mutations in AGP from plants other than maize that correspond to the position of mutations in maize AGP as disclosed herein. Thus, the present invention encompasses polynucleotides that encode mutant AGP of plants other than maize, including, but not limited to, wheat, barley, oats, and rice, that confers increased heat stability when expressed in the plant.

Single amino acid mutations in AGP that confer heat stability, and methods for producing and selecting for such mutations, are disclosed in U.S. Pat. No. 6,069,300 and published international applications WO 99/58698 and WO 98/22601. Typically, a plasmid comprising a polynucleotide coding for the SH2 subunit of maize AGP was mutagenized, placed into mutant *E. coli* glg $C^{-1}$ cells expressing the BT2 subunit, and the cells grown at 42° C. to select for mutants that could produce glycogen at that temperature. Several mutants, termed heat stable (HS) mutants, were isolated. Crude extracts of these mutants were prepared and the heat stability of the resulting AGP was monitored. The single amino acid substitution mutants retained between 8–59% of their activity after incubation at 60° C. for five minutes. In addition, total enzymatic activity of the mutant maize endosperm AGP before heat treatment was elevated about two- to three-fold in several of the mutants.

Multiple heat stability conferring mutations can easily be combined within one subunit. For example, different unique restriction sites that divide the coding regions of Sh2 into three distinct fragments can be used. Where appropriate, mutation combinations can be generated by subcloning the corresponding fragment containing the added mutation. If two mutations are in close proximity, then site-directed mutagenesis can be used to engineer such combinations. One method for site specific mutations involves PCR, mutagenic primer, and the use ofDpnI restriction endonuclease. Primers can be constructed to contain the mutation in the 5' end, and used to PCR amplify using the proofreading polymerase Vent. Amplified DNA can then be digested with DpnI. Parental DNA isolated from *E. coli* is methylated and hence susceptible to DpnI. Digested DNA is size fractionated by gel electrophoresis, ligated, and cloned into the expression vectors. Mutations are confirmed by sequence analysis and transformed into the AC70R1-504 strain carrying the wild type small subunit. Combinatorial mutants can then be analyzed.

The subject invention also concerns the mutant polypeptides, encoded by the subject polynucleotides, having the amino acid substitutions described herein. In a preferred embodiment, the mutant polypeptides are from maize.

The subject invention also concerns heat stable mutants of AGP of the present invention combined with heat stable mutations in the small subunit of the enzyme. Mutations in the small subunit of AGP that confer heat stability to the enzyme can also be readily prepared and identified using the methods described in U.S. Pat. No. 6,069,300 and published international applications WO 99/58698 and WO 98/22601. Heat stable mutants of the small subunit can be co-expressed with the mutants of the present invention to further enhance the stability of an AGP enzyme.

Plants and plant tissue bred to contain or transformed with the mutant polynucleotides of the invention, and expressing the polypeptides encoded by the polynucleotides, are also contemplated by the present invention. Plants and plant tissue expressing the mutant polynucleotides produce tissues that have, for example, lower heat-induced loss in weight or yield when subjected to heat stress during development. Plants within the scope of the present invention include monocotyledonous plants, such as rice, wheat, barley, oats, sorghum, maize, lilies, and millet, and dicotyledonous plants, such as peas, alfalfa, chickpea, chicory, clover, kale, lentil, prairie grass, soybean, tobacco, potato, sweet potato, radish, cabbage, rape, apple trees, and lettuce. In a particularly preferred embodiment, the plant is a cereal. Cereals to which this invention applies include, for example, maize, wheat, rice, barley, oats, rye, and millet.

The subject invention also concerns methods for producing and identifying polynucleotides and polypeptides contemplated within the scope of the invention. In one embodiment, gene mutation, followed by selection using a bacterial expression system, can be used to isolate polynucleotide molecules that encode plant AGP subunits that possess mutations that can alleviate heat-induced loss in starch synthesis in plants. Individual amino acid substitutions can be combined into one subunit as described herein.

The subject invention further concerns plants and plant tissue that comprise a polynucleotide of the present invention that encodes a mutant polypeptide of the invention. In a preferred embodiment, the plant or plant tissue has an AGP mutant gene of the invention incorporated into its genome. Other alleles that confer advantageous phenotypes can also be incorporated into a plant genome. In a preferred embodiment, the plant is a cereal plant. More preferably, the plant is *Zea mays*. Plants having an AGP mutant gene can be grown from seeds that comprise a mutant gene in their genome. In addition, techniques for transforming plants with a gene, such as *Agrobacterium* infection, biolistic methods, etc., are known in the art.

Because of the degeneracy of the genetic code, a variety of different polynucleotide sequences can encode each of the variant AGP polypeptides disclosed herein. In addition, it is well within the skill of a person trained in the art to create alternative polynucleotide sequences encoding the same, or essentially the same, polypeptides of the subject invention. These variant or alternative polynucleotide sequences are within the scope of the subject invention. As used herein, references to "essentially the same" sequence refers to sequences which encode amino acid substitutions, deletions, additions, or insertions which do not materially alter the functional activity of the polypeptide encoded by the AGP mutant polynucleotide described herein.

As used herein, the terms "nucleic acid" and "polynucleotide sequence" refer to a deoxyribonucleotide or ribonucleotide polymer in either single- or double-stranded form, and unless otherwise limited, would encompass known analogs of natural nucleotides that can function in a similar manner as naturally-occurring nucleotides. The polynucleotide sequences include both the DNA strand sequence that is transcribed into RNA and the RNA sequence that is translated into protein. The polynucleotide sequences include both full-length sequences as well as shorter sequences derived from the full-length sequences. It is understood that a particular polynucleotide sequence includes the degenerate codons of the native sequence or sequences which may be introduced to provide codon preference in a specific host cell. Allelic variations of the exemplified sequences also come within the scope of the subject invention. The polynucleotide sequences falling within the scope of the subject invention further include sequences which specifically hybridize with the exemplified sequences. The polynucleotide includes both the sense and antisense strands as either individual strands or in the duplex.

Substitution of amino acids other than those specifically exemplified in the mutants disclosed herein are also contemplated within the scope of the present invention. Amino acids can be placed in the following classes: non-polar, uncharged polar, basic, and acidic. Conservative substitutions whereby a mutant AGP polypeptide having an amino acid of one class is replaced with another amino acid of the same class fall within the scope of the subject invention so long as the mutant AGP polypeptide having the substitution still retains increased heat stability relative to a wild type polypeptide. Table 2 below provides a listing of examples of amino acids belonging to each class.

TABLE 2

| Class of Amino Acid | Examples of Amino Acids |
| --- | --- |
| Nonpolar | Ala, Val, Leu, Ile, Pro, Met, Phe, Trp |
| Uncharged Polar | Gly, Ser, Thr, Cys, Tyr, Asn, Gln |
| Acidic | Asp, Glu |
| Basic | Lys, Arg, His |

For example, substitution of the tyrosine at position 333 in the HS 33, HS 7+3, HS 6+3, and HS 7+6+3 mutants with other amino acids, such as glycine, serine, threonine, cysteine, asparagine, and glutamine, are encompassed within the scope of the invention. Also specifically contemplated within the scope of the invention is substitution of either a phenylalanine or a methionine at position 333 in the AGP large subunit. Thus, a combination of phenylalanine or methionine at position 333 with either a valine at position 177 or a valine at position 396, or both, is specifically contemplated by the present invention. Similarly, substitution of the valine at positions 177 and 396 in the RTS 48-2, RTS 60-1, HS 7+3, HS 6+3, HS 7+6, and HS 7+6+3 mutants with other amino acids such as leucine, isoleucine, proline, methionine, phenylalanine, and tryptophan, is within the scope of the invention. Amino acid substitutions at positions other than the site of the heat stable mutation are also contemplated within the scope of the invention so long as the polypeptide retains or confers increased heat stability relative to wild type polypeptides.

Polynucleotides and proteins of the subject invention can also be defined in terms of more particular identity and/or similarity ranges with those exemplified herein. The sequence identity will typically be greater than 60%, preferably greater than 75%, more preferably greater than 80%, even more preferably greater than 90%, and can be greater than 95%. The identity and/or similarity of a sequence can be 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% as compared to a sequence exemplified herein. Unless otherwise specified, as used herein percent sequence identity and/or similarity of two sequences can be determined using the algorithm of Karlin and Altschul (Karlin and Altschul [1990] *Proc. Natl. Acad. Sci. USA* 87:2264–2268), modified as in Karlin and Altschul (Karlin and Altschul [1993] *Proc. Natl. Acad. Sci. USA* 90:5873-5877). Such an algorithm is incorporated into the NBLAST and XBLAST programs of Altschul et al. (Altschul et al. [1990] *J. Mol. Biol.* 215:402–410). BLAST searches can be performed with the NBLAST program, score=100, wordlength=12, to obtain sequences with the desired percent sequence identity. To obtain gapped alignments for comparison purposes, Gapped BLAST can be used as described in Altschul et al. (Altschul et al. [1997] *Nucl. Acids Res.* 25:3389–3402). When utilizing BLAST and Gapped BLAST programs, the default parameters of the respective programs (NBLAST and XBLAST) can be used. See NCBI/NIH website.

The subject invention also concerns polynucleotides which encode fragments of the full length mutant polypeptide, so long as those fragments retain substantially the same functional activity as full length polypeptide. The fragments of mutant AGP polypeptide encoded by these polynucleotides are also within the scope of the present invention. Fragments of the full length sequence can be prepared using standard techniques known in the art.

The subject invention also contemplates those polynucleotide molecules encoding starch biosynthesis enzymes having sequences which are sufficiently homologous with the wild type sequence so as to permit hybridization with that sequence under standard stringent conditions and standard methods (Maniatis, T., E. F. Fritsch, J. Sambrook [1982] *Molecular Cloning: A Laboratory Manual,* Cold Spring Harbor Laboratory, Cold Spring Harbor, N.Y.). As used herein, "stringent" conditions for hybridization refers to conditions wherein hybridization is typically carried out overnight at 20–25° C. below the melting temperature (Tm) of the DNA hybrid in 6×SSPE, 5× Denhardt's solution, 0.1% SDS, 0.1 mg/ml denatured DNA. The melting temperature is described by the following formula (Beltz, G. A., K. A. Jacobs, T. H. Eickbush, P. T. Cherbas, and F. C. Kafatos [1983] *Methods of Enzymology,* R. Wu, L. Grossman and K. Moldave [eds.] Academic Press, New York 100:266–285):

Tm=81.5° C.+16.6 Log[Na+]+0.41(% G+C)−0.61(% formamide)-600/length of duplex in base pairs.

Washes are typically carried out as follows:

(1) Twice at room temperature for 15 minutes in 1×SSPE, 0.1% SDS (low stringency wash).

(2) Once at Tm-20° C. for 15 minutes in 0.2×SSPE, 0.1% SDS (moderate stringency wash).

The polynucleotide molecules of the subject invention can be used to transform plants to express the mutant heat stable enzyme in those plants. In addition, the polynucleotides of the subject invention can be used to express the recombinant variant enzyme. They can also be used as a probe to detect related enzymes. The polynucleotides can also be used as DNA sizing standards.

The polynucleotide molecules of the subject invention also include those polynucleotides that encode starch biosynthesis enzymes, such as AGP enzymes, that contain mutations that can confer increased seed weight, in addition to enhanced heat stability, to a plant expressing these mutants. The combination of a heat stabilizing mutation, such as, for example, Sh2-HS 7+6 or Sh2-HS 7+3, with a mutation conferring increased seed weight, e.g., Rev6, in a polynucleotide that encodes the large subunit of maize AGP is specifically contemplated in the present invention. U.S. Pat. Nos. 5,589,618 and 5,650,557 disclose polynucleotides (e.g., Rev6) that encode mutations in the large subunit of AGP that confer increased seed weight in plants that express the mutant polypeptide.

Mutations in the AGP subunits that confer heat stability can be combined according to the subject invention with phosphate insensitive mutants of maize, such as the Rev6 mutation, to enhance the stability of the Rev6 encoded large subunit.

It is expected that enzymic activity of SSS will be impaired at higher temperatures as observed with AGP. Thus, mutagenized forms of SSS can be expressed under increased thermal conditions (42° C.), to isolate heat stable variants in accordance with the methods described herein. These heat stable mutagenized forms of SSS are further aspects of the subject invention.

The subject invention also concerns methods for increasing yield characteristics of plants under conditions of heat stress by incorporating a polynucleotide of the present invention that comprises a mutation in a starch biosynthesis enzyme that confers increased stability or resistance to heat stress conditions and a mutation that confers increased yield characteristics on the plant. Increased yield characteristics include, for example, increased seed number, increased seed weight, increased plant biomass, and increased Harvest Index.

All patents, patent applications, provisional applications, and publications referred to or cited herein are hereby incorporated by reference in their entirety to the extent they are not inconsistent with the explicit teachings of this specification.

Following are examples which illustrate procedures for practicing the invention. These examples should not be construed as limiting. All percentages are by weight and all solvent mixture proportions are by volume unless otherwise noted.

EXAMPLE 1

Testing of Maize Endosperm ADP-Glucose Pyrophosphorylases having Multiple Amino Acid Mutations Expression of Maize Endosperm ADP-glucose Pyrophosphorylases. 10-ml aliquots of Luria broth (75 g/mL of spectinomycin and 50 g/mL of kanamycin) were inoculated from glycerol stocks of AC70R1–504 *E. coli* cells expressing either maize endosperm or potato tuber ADP-glucose pyrophosphorylase, and grown overnight at 37C with shaking at 220 rpm. These cultures were used to inoculate 250 mL of Luria broth (75 g/mL of spectinomycin and 50 g/mL of kanamycin). Cultures were grown to an $OD_{600}$=0.55 at 37C with shaking at 220 rpm. Cultures were induced with 0.2 mM isopropyl-D-thiogalactoside and 0.02 mg/mL nalidixic acid for 7 hrs at room temperature with shaking at 220 rpm. Cells were harvested at 3500 rpm for 10 min at 4C. Cell pellets were resuspended in 800L of extraction buffer: 50 mM HEPES, pH 7.5,5 mM $MgCl_2$, 5 mM EDTA, 20% sucrose, and 30% ammonium sulfate. DTT (1 mM), 50 g/ml lysozyme, 1 g/mL pepstatin, 1 g/mL leupeptin, 1 g/mL antipain, 10 g/mL chymostatin, 1 mM phenylmethylsulfonyl fluoride, and 1 mM benzamidine were added to extraction buffer just before use. Lysates were sonicated three times for three seconds with incubation on ice between sonications. Samples were centrifuged for 1 min at 13,000 rpm at 4C. Supernatants were removed and aliquoted for assays.

Combination of Individual Mutations. A subcloning strategy was designed to study the effects of the mutations in combination with HS 33, and with each other. To combine the reversion mutations of RTS 48-2 and RTS 60-1, the plasmids containing each reversion mutation (the temperature sensitive parental mutations were removed prior to combining mutations) were digested with Eco RV and a 339 bp fragment of RTS 48-2 was exchanged for the corresponding fragment of RTS 60-1 (FIG. 3). The resulting plasmid was designated Sh2-HS 7+6. A similar strategy was used to combine the reversion mutation of RTS 48-2 with the mutation identified in HS 33. Plasmids containing the mutations were digested with Eco RV and a 339 bp fragment of RTS 48-2 was exchanged for the corresponding fragment of HS 33. The resulting plasmid was designated Sh2-HS 7+3. To combine the reversion mutation of RTS 60-1 with the mutation identified in HS 33, plasmids containing the mutations were digested with Mun I/Kpn I and a 390 bp fragment of RTS 60-1 was exchanged for the corresponding fragment of HS 33 (FIG. 3). The resulting plasmid was designated Sh2-HS 6+3. In order to combine the reversion mutations of RTS 60-1 and RTS 48-2 with the mutation identified in HS 33, plasmid Sh2-HS 6+3 and a plasmid containing the reversion mutation RTS 48-2 were digested with Eco RV and a 339 bp fragment of RTS 48-2 was exchanged for the corresponding fragment of Sh2-HS 6+3. The resulting plasmid was designated Sh2-HS 7+6+3.

Final sequencing of all plasmids was performed using six primers to cover the entire Sh2 coding region in both directions. Primers used are as follows:

LHBB1 (5'→3'): 5'-CGACTCACTATAGGGAGACC-3' (SEQ ID NO. 5);

LH27 (5'→3'): 5'-CCCTATGAGTAACTG-3' (SEQ ID NO. 6);
LH9 (5'→3'): 5'-TATACTCAATTACAT-3' (SEQ ID NO. 7);
LHBB2 (3'→5'): 5'-GTGCCACCTGACGTCTAAG-3' (SEQ ID NO. 8);
LH2135 (3'→5'): 5'-CAGAGCTGACACGTG-3' (SEQ ID NO. 9);
LH32 (3'→5'): 5'-AAGCTGATCGCCACTC-3' (SEQ ID NO. 10).

Heat Treatment of ADP-glucose Pyrophosphorylase. Wild type (sh2) and mutant ADP-glucose pyrophosphorylase containing a single amino acid mutation (HS 33, RTS 48-2, RTS 60-1) and multiple mutation (HS 7+3, i.e., RTS 48-2 plus HS 33; HS 6+3, i.e., RTS 60-1 plus HS 33; and HS 7+6, i.e., RTS 48-2 plus RTS 60-1) amino acid changes were tested for enzyme activity before and after heat treatment. Heat treatment consisted of incubation of the test protein at 60° C. for 5 minutes.

The percentage of activity remaining after heat treatment at 60° C. for 5 min is presented in Table 3. Genotypes in the data set are Sh2 wild type, HS 33, RTS 60-1 (reversion mutation only), RTS 48-2 (reversion mutation only), Sh2-HS 7+6, Sh2-HS 6+3, Sh2-HS 7+3, and Sh2-HS 7+6+3.

TABLE 3

Percent Activity Remaining After Heat Treatment

| Enzyme | % Activity | SEM[a] | N[b] |
|---|---|---|---|
| Sh2 wt | 32 | 11 | 3 |
| HS 33 | 69 | 7 | 7 |
| RTS 60-1 | 61 | 13* | 2 |
| RTS 48-2 | 64 | 6 | 3 |
| Sh2-HS 7 + 6 | 77 | 21* | 2 |
| Sh2-HS 6 + 3 | 69 | 9 | 3 |
| Sh2-HS 7 + 3 | 83 | 8 | 3 |
| Sh2-HS 7 + 6 + 3 | 72 | 11 | 3 |

[a]standard error of the mean
[b]number of experimental replicates
*represents range, rather than S.E.M.

Activity before heat treatment for Sh2 wild type, HS 33, RTS 60-1, RTS 48-2, Sh2-HS 7+6, Sh2-HS 6+3, Sh2-HS 7+3, and Sh2-HS 7+6+3 is shown in Table 4. HS 33 has 2.1 fold more activity than does Sh2 wild type. Both RTS 48-2 and RTS 60-1 show a 1.4 fold increase in activity. Their double mutant contains a 1.9 fold increase in activity. While the combination of the two mutants increases activity, the double mutant does not experience synergistic effects. The mutation of RTS 60-1 when combined with that of HS 33 experiences an additive effect, raising activity 3.4 fold compared to Sh2 wild type. The mutation of RTS 48-2 in combination with that of HS 33 exhibits a slightly smaller increase to 2.9 fold. Interestingly, the triple mutant shows a slightly greater increase than either second-site reversion mutation alone, but less than the double mutant between second-site revertants.

TABLE 4

Fold Increase in Activity

| Enzyme | Fold increase | Range | N[b] |
|---|---|---|---|
| Sh2 wt | n/a | n/a | n/a |
| HS 33 | 2.1 | 0.2[a] | 3 |
| RTS 60-1 | 1.4 | 0 | 1 |
| RTS 48-2 | 1.4 | 0 | 1 |

TABLE 4-continued

Fold Increase in Activity

| Enzyme | Fold increase | Range | N[b] |
|---|---|---|---|
| Sh2-HS 7 + 6 | 1.9 | 0.2 | 2 |
| Sh2-HS 6 + 3 | 3.4 | 0 | 1 |
| Sh2-HS 7 + 3 | 2.9 | 0.1 | 2 |
| Sh2-HS 7 + 6 + 3 | 1.8 | 0.1 | 2 |

[a]standard error of the mean
[b]number of experimental replicates
n/a not applicable ADP-glucose Pyrophosphorylase Assays. To obtain quantitative data for the mutants described above, activity was measured with the synthesis (forward) assay that measures incorporation Of [$^{14}$C]glucose-1-P into the sugar nucleotide ADP-glucose. Assays were performed on crude enzyme extracts prepared as described below.

The ADP-glucose synthesis reaction measures incorporation of [$^{14}$C]glucose-1-P into ADP-Glucose. The reaction mixture contained 80 mM HEPES, pH 7.5m, 1 mM glucose-1-P, 4 MM MgCl$_2$, 0.5 mg mL$^{-1}$; bovine serum albumin, 10 mM 3-PGA, and 15,000 cpm of [$^{14}$C]glucose-1-P. Reaction volume was 50 mL. Assays were initiated by addition of 1.5 mM ATP. Reaction was incubated for 30 min at 37° C. and terminated by boiling for 2 min. Unincorporated glucose-1-P was cleaved by addition of 0.3 U of bacterial alkaline phosphatase (Worthington Biochemical Corporation, Lakewood, N.J.) and incubation for 2.5 h at 37° C. A 20 mL aliquot of the reaction mixture was spotted on DEAE paper, washed with distilled water three times, dried, and quantified in a liquid scintillation counter.

Additional results for single and double mutants are shown in FIG. 2. For the combination mutant Sh2-HS 7+6 (RTS 48-2 plus RTS 60-1) and the combination mutant Sh2-HS 6+3 (RTS 60-1 plus HS 33), the numbers given are the average of data from 3 dilutions of the enzyme (in duplicate), multiplied by their dilution factor, minus background. For the combination Sh2-HS 7+3 (RTS 48-2 plus HS 33) mutant, the numbers given are the average of 2 dilutions of the enzyme (in duplicate), multiplied by their dilution factor, minus background. Graphic representation of the numbers was performed using Microsoft Excel.

EXAMPLE 2

Combination of Heat Stability Mutations with Rev6

According to the subject invention, the heat stable mutations can be combined with a mutation associated with increased seed weight, such as, for example, the Rev6 mutation. The goal is to maintain the desired phosphate insensitivity characteristic of Rev6 while enhancing its stability. Mutants comprising heat stable mutations combined with Rev6 mutation can be constructed and confirmed as described herein. These "combination" mutants can be transformed into AC70R1–504 carrying the wild type small subunit. Increased heat stability can be easily identified by a positive glycogen staining on a low glucose media. Rev6 does not stain when grown on this media. Initially all mutant combinations can be screened enzymatically for maintenance of phosphate insensitivity, and only combinations that maintain phosphate insensitivity are further analyzed.

It should be understood that the examples and embodiments described herein are for illustrative purposes only and that various modifications or changes in light thereof will be suggested to persons skilled in the art and are included within the spirit and purview of this application and the scope of the appended claims.

We claim:

1. A polynucleotide encoding a mutant large subunit of a maize endosperm ADP-glucose pyrophosphorylase polypeptide, or a biologically-active fragment of said mutant polypeptide, wherein said mutant polypeptide comprises amino acid mutations at two or more sites in the amino acid sequence of said polypeptide and wherein when said mutant polypeptide is expressed with a small subunit of ADP-glucose pyrophosphorylase to form a mutant ADP-glucose pyrophosphorylase enzyme, said mutant enzyme, or a biologically-active fragment of said mutant enzyme, exhibits increased heat stability relative to wild typo maize endosperm ADP-glucose pyrophosphorylase enzyme, wherein said mutant polypeptide encoded by said polynucleotide comprises a first amino acid mutation wherein the histidine amino acid in said maize polypeptide at position 333 in the amino acid sequence or the wild type large subunit of ADP-glucose pyrophosphorylase polypeptide of maize is replaced by an amino acid that confers said increased heat stability on said mutant enzyme, and wherein said mutant polypeptide encoded by said polynucleotide comprises a second amino acid mutation wherein the alanine amino acid in said maize polypeptide at position 177 in the amino acid sequence of the wild type large subunit of ADP-glucose pyrophosphorylase polypeptide of maize is replaced by an amino acid that confers said increased heat stability on said mutant enzyme.

2. The polynucleotide according to claim 1, wherein the amino acid that replaces histidine at position number 333 is selected from the group consisting of tyrosine, phenylalanine, methionine, glycine, serine, threonine, cysteine, asparagine, and glutamine.

3. The polynucleotide according to claim 1, wherein the amino acid that replaces histidine at position number 333 is tyrosine.

4. The polynucleotide according to claim 1, wherein the amino acid that replaces histidine at position number 333 is phenylalanine.

5. The polynucleotide according to claim 1, wherein the amino acid that replaces histidine at position number 333 is methionine.

6. The polynucleotide according to claim 1, wherein the amino acid that replaces alanine at position number 177 is a proline.

7. The polynucleotide according to claim 1, wherein the amino acid that replaces alanine at position number 177 is a valine.

8. The polynucleotide according to claim 2, wherein the amino acid that replaces alanine at position number 177 is a proline.

9. The polynucleotide according to claim 2, wherein the amino acid that replaces alanine at position number 177 is a valine.

10. The polynucleotide according to claim 3, wherein the amino acid that replaces alanine at position number 177 is a proline.

11. The polynucleotide according to claim 3, wherein the amino acid that replaces alanine at position number 177 is a valine.

12. The polynucleotide according to claim 4, wherein the amino acid that replaces alanine at position number 177 is a proline.

13. The polynucleotide according to claim 4, wherein the amino acid that replaces alanine at position number 177 is a valine.

14. The polynucleotide according to claim 5, wherein the amino acid that replaces alanine at position number 177 is a proline.

15. The polynucleotide according to claim 5, wherein the amino acid that replaces alanine at position number 177 is a valine.

16. A polynucleotide encoding a mutant large subunit of a plant maize endosperm ADP-glucose pyrophosphorylase polypeptide, or a biologically-active fragment of said mutant polypeptide, wherein said mutant polypeptide comprises amino acid mutations at two or more sites in the amino acid sequence of said polypeptide and wherein when said mutant polypeptide is expressed with a small subunit of ADP-glucose pyrophosphorylase to form a mutant ADP-glucose pyrophosphorylase enzyme, said mutant enzyme, or a biologically-active fragment of said mutant enzyme, exhibits increased heat stability relative to wild type maize endosperm ADP-glucose pyrophosphorylase enzyme, wherein said mutant polypeptide encoded by said polynucleotide comprises a first amino acid mutation wherein the histidine amino acid in said maize polypeptide at position 333 in the amino acid sequence of the wild type large subunit of ADP-glucose pyrophosphorylase polypeptide of maize is replaced by an amino acid that confers said increased heat stability on said mutant enzyme, and wherein said mutant polypeptide encoded by said polynucleotide comprises a second amino acid mutation wherein the alanine amino acid in said maize polypeptide at position 396 in the amino acid sequence of the wild type large subunit of ADP-glucose pyrophosphorylase polypeptide of maize is replaced by an amino acid that confers said increased heat stability on said mutant enzyme.

17. The polynucleotide according to claim 16, wherein the amino acid that replaces histidine at position number 333 is selected from the group consisting of tyrosine, phenylalanine, methionine, glycine, serine, threonine, cysteine, asparagine, and glutamine.

18. The polynucleotide according to claim 16, wherein the amino acid replaces histidine at position number 333 is tyrosine.

19. The polynucleotide according to claim 16, wherein the amino acid that replaces histidine at position number 333 is phenylalanine.

20. The polynucleotide according to claim 16, wherein the amino acid that replaces histidine at position number 333 is methionine.

21. The polynucleotide according to claim 16, wherein the amino acid that replaces alanine at position number 396 is a valine.

22. The polynucleotide according to claim 17, wherein the amino acid that replaces alanine at position number 396 is a valine.

23. The polynucleotide according to claim 18, wherein the amino acid that replaces alanine at position number 396 is a valine.

24. The polynucleotide according to claim 19, wherein the amino acid that replaces alanine at position number 396 is a valine.

25. The polynucleotide according to claim 20, wherein the amino acid that replaces alanine at position number 396 is a valine.

26. A method for increasing resistance of a plant to heat stress conditions, said method comprising incorporating the polynucleotide of claim 1, the polynucleotide of claim 2, the polynucleotide of claim 3, the polynucleotide of claim 4, the polynucleotide of claim 5, the polynucleotide of claim 6, the polynucleotide of claim 10, the polynucleotide of claim 11, the polynucleotide of claim 12, the the polynucleotide of claim 7, the polynucleotide of claim 8, the polynucleotide of claim 9, the polynucleotide of claim 13, the polynucleotide of claim 14, the polynucleotide of claim 15, the polynucleotide of claim 16, the polynucleotide of claim 17, the polynucleotide of claim 18, the polynucleotide of claim 19, the polynucleotide of claim 20, the polynucleotide of claim 21, the polynucleotide of claim 22, the polynucleotide of claim 23, the polynucleotide of claim 24, the polynucleotide of claim 25, in said plant and expressing the protein encoded by said polynucleotide.

27. The method according to claim 26, wherein said plant is a monocotyledonous plant.

28. The method according to claim 27, wherein said monocotyledonous plant is selected from the group consisting of rice, wheat, barley, oat, sorghum, maize, lily, and millet.

29. The method according to claim 26, wherein said plant is *Zea mays*.

30. The method according to claim 26, wherein said plant is a dicotyledonous plant.

31. The method according to claim 30, wherein said dicotyledonous plant is selected from the group consisting of peas, alfalfa, chickpea, chicory, clover, kale, lentil, prairie grass, soybean, tobacco, potato, sweet potato, radish, cabbage, rape, apple trees, and lettuce.

32. A plant or plant tissue comprising the polynucleotide of claim 1, polynucleotide of claim 2, the polynucleotide of claim 3, the polynucleotide of claim 4, the polynucleotide of claim 5, the polynucleotide of claim 6, the polynucleotide of claim 7, the polynucleotide of claim 8, the polynucleotide of claim 9, the polynucleotide of claim 10, the polynucleotide of claim 11, the polynucleotide of claim 12, the polynucleotide of claim 13, the polynucleotide of claim 14, the polynucleotide of claim 15, the polynucleotide of claim 16, the polynucleotide of claim 17, the polynucleotide of claim 18, the polynucleotide of claim 19, the polynucleotide of claim 20, the polynucleotide of claim 21, the polynucleotide of claim 22, the polynucleotide of claim 23, the polynucleotide of claim 24, or the polynucleotide of claim 25.

33. The plant or plant tissue according to claim 32, wherein said plant or plant tissue is monocotyledonous.

34. The plant or plant tissue according to claim 33, wherein said monocotyledonous plant or plant tissue is selected from the group consisting of rice, wheat, barley, oat, sorghum, maize, lily, and millet.

35. The plant or plant tissue according to claim 32, wherein said plant is *Zea mays* or said plant tissue is from *Zea mays*.

36. The plant or plant tissue according to claim 32, wherein said plant or plant tissue is dicotyledonous.

37. The plant or plant tissue according to claim 36, wherein said dicotyledonous plant or plant tissue is selected from the group consisting of peas, alfalfa, chickpea, chicory, clover, kale, lentil, prairie grass, soybean, tobacco, potato, sweet potato, radish, cabbage, rape, apple trees, and lettuce.

38. The plant tissue according to claim 32, wherein said plant tissue is a seed.

* * * * *

UNITED STATES PATENT AND TRADEMARK OFFICE
CERTIFICATE OF CORRECTION

PATENT NO. : 6,969,783 B2
DATED : November 29, 2005
INVENTOR(S) : L. Curtis Hannah et al.

It is certified that error appears in the above-identified patent and that said Letters Patent is hereby corrected as shown below:

Column 1,
Line 51, "*Physol. Plant.* 59-66)." should read -- *Physiol. Plant.* 95:59-66). --.

Column 4,
Line 31, "AGP, designated as glyc." should read -- AGP, designated as *gly*C. --.
Line 32, "E. *coli*, known as glyc-16," should read -- E. *coli*, known as *gly*C-16, --.

Column 6,
Lines 42-43, "enzyme activities.
            The mutant enzymes" should read
-- enzyme activities. The mutant enzymes --.
Line 46, "enzyme activities. One aspect of" should read
-- enzyme activities.
      One aspect of --.
Line 52, "bythe subject" should read -- by the subject --.

Column 7,
Line 65, "mutant E. *coli* glg $C^{-1}$ cells" should read -- mutant E. *coli* glg $C^-$ cells --.

Column 8,
Line 17, "use ofDpnI restriction" should read -- use of *Dpn*I restriction --.

Column 14,
Line 17, "incorporation Of" should read -- incorporation of --.
Line 23, "4 MM MgCl$_2$" should read -- 4 mM MgCl$_2$ --.

UNITED STATES PATENT AND TRADEMARK OFFICE
CERTIFICATE OF CORRECTION

PATENT NO. : 6,969,783 B2
DATED : November 29, 2005
INVENTOR(S) : L. Curtis Hannah et al.

It is certified that error appears in the above-identified patent and that said Letters Patent is hereby corrected as shown below:

Column 25,
Line 57, "a plant maize endosperm" should read -- a maize endosperm --.

Signed and Sealed this

Twenty-eighth Day of March, 2006

JON W. DUDAS
*Director of the United States Patent and Trademark Office*

UNITED STATES PATENT AND TRADEMARK OFFICE
CERTIFICATE OF CORRECTION

| | | |
|---|---|---|
| PATENT NO. | : 6,969,783 B2 | Page 1 of 1 |
| APPLICATION NO. | : 10/099031 | |
| DATED | : November 29, 2005 | |
| INVENTOR(S) | : L. Curtis Hannah, Thomas W. Greene and Brian Burger | |

It is certified that error appears in the above-identified patent and that said Letters Patent is hereby corrected as shown below:

Column 26,
Lines 57-58, "the polynucleotide of claim 24, the polynucleotide of claim 25" should read -- the polynucleotide of claim 24, or the polynucleotide of claim 25 --

Signed and Sealed this

Twenty-first Day of November, 2006

JON W. DUDAS
*Director of the United States Patent and Trademark Office*